(12) United States Patent
Ehteshami

(10) Patent No.: US 11,684,482 B2
(45) Date of Patent: Jun. 27, 2023

(54) SPONDYLOLISTHESIS SYSTEM AND METHODS

(71) Applicant: ADDITIVE IMPLANTS, INC., Phoenix, AZ (US)

(72) Inventor: John R. Ehteshami, Paradise Valley, AZ (US)

(73) Assignee: Additive Implants, Inc., Phoenix, AZ (US)

( * ) Notice: Subject to any disclaimer, the term of this patent is extended or adjusted under 35 U.S.C. 154(b) by 330 days.

(21) Appl. No.: 16/717,840

(22) Filed: Dec. 17, 2019

(65) Prior Publication Data

US 2020/0197050 A1 Jun. 25, 2020

Related U.S. Application Data

(60) Provisional application No. 62/783,195, filed on Dec. 20, 2018.

(51) Int. Cl.
*A61F 2/44* (2006.01)
*A61F 2/46* (2006.01)
*A61F 2/30* (2006.01)

(52) U.S. Cl.
CPC .............. *A61F 2/4465* (2013.01); *A61F 2/44* (2013.01); *A61F 2/4455* (2013.01); *A61F 2/4611* (2013.01); *A61F 2002/30535* (2013.01)

(58) Field of Classification Search
CPC ................. A61F 2/4611; A61F 2/4465–2/447
See application file for complete search history.

(56) References Cited

U.S. PATENT DOCUMENTS

| | | |
|---|---|---|
| 5,609,635 A | 3/1997 | Michelson |
| 6,395,035 B2 | 5/2002 | Bresina et al. |
| 6,592,624 B1 | 7/2003 | Fraser |
| 6,723,126 B1 | 4/2004 | Berry |

(Continued)

OTHER PUBLICATIONS

International Search Report and Written Opinion dated Apr. 21, 2020 for corresponding International Application No. PCT/US2019/067252.

(Continued)

*Primary Examiner* — Julianna N Harvey
(74) *Attorney, Agent, or Firm* — David Meibos; Maywood IP Law

(57) ABSTRACT

An intervertebral implant for spondylolisthesis correction includes a superior side with serrations angled superiorly and toward the implant insertion direction, an inferior side with serrations angled inferiorly and opposite the implant insertion direction, and an instrument connection feature. An instrument for connection to the implant includes an implant connection feature movable between unlocked and locked states, and a friction-reducing feature movable between disengaged and engaged states. The instrument has a first state, in which the implant connection feature is in the unlocked state and the friction-reducing feature is in the disengaged state; a second state, in which the implant connection feature is in the locked state and the friction-reducing feature is in the engaged state; and a third state, in which the implant connection feature is in the locked state and the friction-reducing feature is in the disengaged state. Methods of apparatus assembly and surgery are disclosed.

22 Claims, 10 Drawing Sheets

(56) References Cited

U.S. PATENT DOCUMENTS

| | | |
|---|---|---|
| 6,979,353 B2 | 12/2005 | Bresina |
| 7,238,203 B2 | 7/2007 | Bagga et al. |
| 7,867,277 B1 | 1/2011 | Tohmeh |
| 7,918,891 B1 | 4/2011 | Curran et al. |
| 10,299,938 B1 | 5/2019 | Ehteshami |
| 2003/0040802 A1 | 2/2003 | Errico et al. |
| 2008/0154377 A1* | 6/2008 | Voellmicke ........... A61F 2/4611 623/17.16 |
| 2010/0057206 A1 | 3/2010 | Duffield et al. |
| 2010/0076557 A1* | 3/2010 | Miller .................. A61F 2/4611 606/90 |
| 2010/0114105 A1* | 5/2010 | Butters ................. A61F 2/447 623/17.11 |
| 2010/0298941 A1 | 11/2010 | Hes et al. |
| 2010/0331982 A1 | 12/2010 | McCombe |
| 2011/0071635 A1 | 3/2011 | Zhang et al. |
| 2012/0095559 A1* | 4/2012 | Woods .................. A61F 2/4455 623/17.11 |
| 2013/0131806 A1 | 5/2013 | Carpenter |
| 2014/0088711 A1 | 3/2014 | Chin et al. |
| 2017/0340453 A1 | 11/2017 | Kaufmann et al. |
| 2017/0348114 A1 | 12/2017 | Jones et al. |
| 2018/0325694 A1 | 11/2018 | Petersheim et al. |
| 2019/0083270 A1 | 3/2019 | Milz et al. |
| 2019/0133783 A1 | 5/2019 | Unger et al. |
| 2019/0343652 A1 | 11/2019 | Petersheim et al. |
| 2019/0350673 A1* | 11/2019 | Kieser ................... A61B 90/39 |
| 2020/0078191 A1 | 3/2020 | Ehteshami et al. |

OTHER PUBLICATIONS

International Search Report and Written Opinion dated Jan. 14, 2021 for corresponding International Application No. PCT/US2020/052412.

* cited by examiner

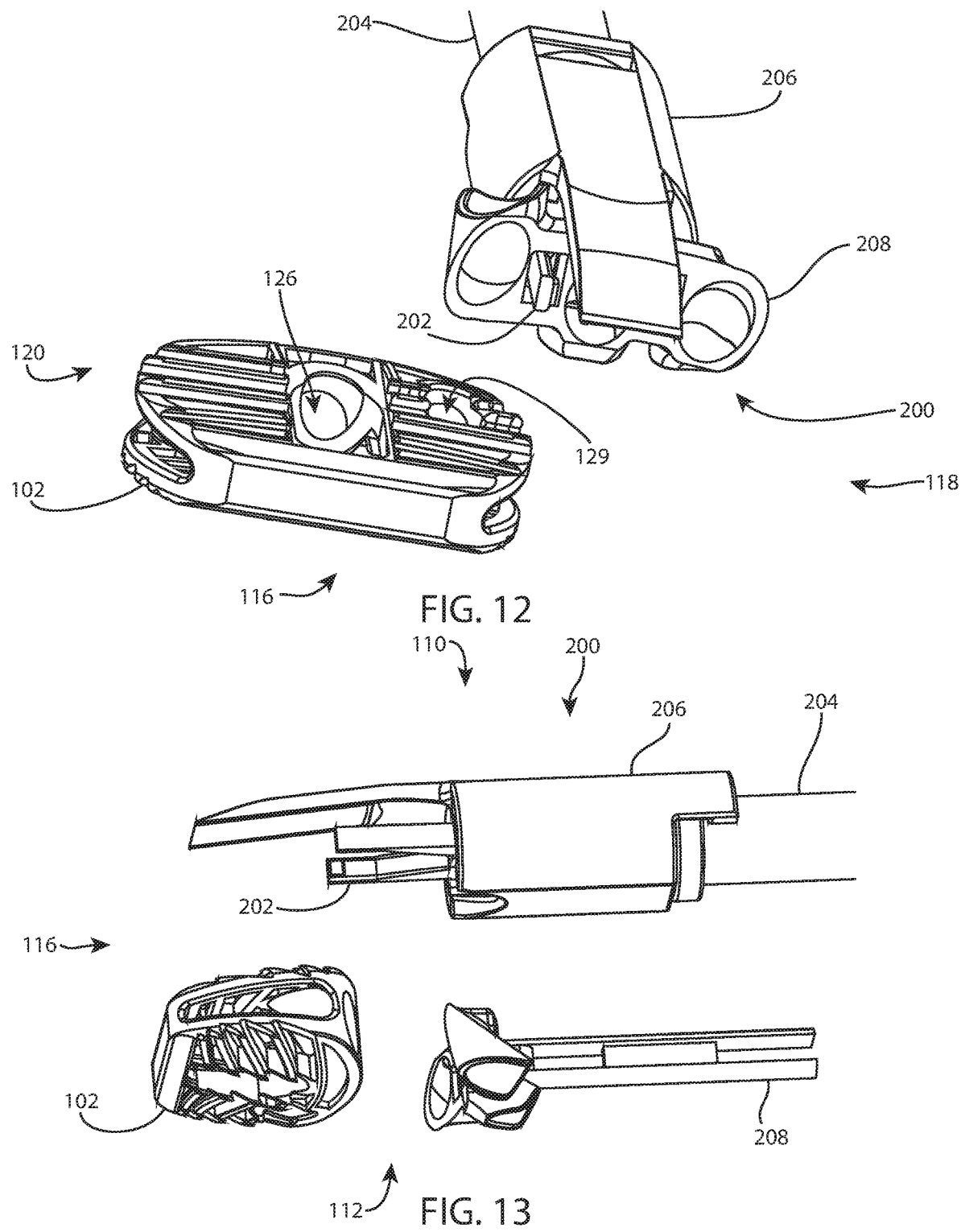

SPONDYLOLISTHESIS SYSTEM AND METHODS

CROSS-REFERENCE TO RELATED APPLICATIONS

The present application claims the benefit of:

U.S. Provisional Patent Application Ser. No. 62/783,195, entitled OPPOSING-SERRATION LUMBAR IMPLANT, INSERTION ASSEMBLY, AND METHOD OF IMPLANTATION; METHOD OF TREATMENT OF SPONDYLOLISTHESIS; LOCKING SCREW AND INSERTION ASSEMBLY, filed Dec. 20, 2018.

The foregoing is incorporated by reference as though set forth herein in its entirety.

TECHNICAL FIELD

The present disclosure relates to implants, instruments, and methods for spinal surgery. More specifically, the present disclosure relates to implants, instruments, and methods for spinal surgery to correct spondylolisthesis, which refers to displacement of a vertebra relative to an adjacent vertebra or sacrum. The implants may resist axial forces, shear forces, and bending moments to stabilize the treated spinal level sufficiently to promote fusion between the vertebrae or vertebra/sacrum. While the current disclosure is made in the context of correcting anterior displacement of a superior vertebra relative to an adjacent inferior vertebra or sacrum, one of skill in the art will appreciate that the principles disclosed herein may be adapted to correct vertebral displacements along other directions, as well as displacements between other bones beyond the spine. Furthermore, the disclosed technology may be applicable to inhibit or prevent implant migration in vivo in the absence of spondylolisthesis.

BACKGROUND

Spondylolisthesis is a spinal condition in which a vertebra displaces out of its normal anatomical position relative to an adjacent vertebra. The displacement may occur anteriorly, posteriorly, to the right or left, or obliquely in any direction in a transverse anatomical plane. Spondylolisthesis may occur due to back injury or trauma, old age, birth defects, or other factors. In one example, a superior vertebra may displace, or slip, anteriorly relative to an inferior vertebra or the sacrum so that an anterior side of the superior vertebra overhangs an anterior side of the inferior vertebra. The displacement may occur in other directions as well. The distance between the normal anatomical location of the superior vertebra relative to the inferior vertebra or sacrum and the displaced location of the superior vertebra relative to the inferior vertebra or sacrum may be referred to as the slip distance. The vertebral displacement may occur together with a fracture of the pars interarticularis, which is the portion of the vertebra located between the inferior and superior articular processes of the facet joints. Spondylolisthesis may cause symptoms such as leg and thigh pain or hamstring stiffness. Surgical treatment may be required to relieve the symptoms by addressing the vertebral displacement (reducing or eliminating the slip distance) and/or stabilizing the pars interarticularis fracture. The superior vertebra may move from a starting position relative to the inferior vertebra to a corrected position that is closer to the normal anatomical position than the starting position was, so that the spondylolisthesis is reduced, or to the normal anatomical position, so that the spondylolisthesis is eliminated.

Anatomical abnormalities, advancing age, injury, and the like can lead to changes in the bones, disks, joints, and ligaments of the spine producing instability that in combination with other factors can lead to pain from nerve root compression, as well as other sources. Under certain circumstances, performing a spinal fusion can stabilize the vertebrae, alleviating pain. This is a procedure that involves joining two or more adjacent vertebrae so that they no longer are able to move relative to each other.

Many prosthetic devices are known for promoting fusion of the spinal vertebrae, and the devices can be classified, in part, based upon the approach to the spine that will be taken by the surgeon: anterior, posterior, lateral, or other. None of the known devices is completely satisfactory in neutralizing or withstanding all the forces and moments that need to be transferred between the adjacent vertebrae. There is a need for implants that are able to resist these forces and torques, resulting in substantially improved surgical outcomes.

SUMMARY

The various systems and methods of the present technology have been developed in response to the present state of the art, and in particular, in response to the problems and needs in the art that have not yet been fully solved by currently available spinal implants.

To achieve the foregoing, and in accordance with the technology as embodied and broadly described herein, an aspect of the technology includes a method for spinal surgery in an intervertebral space between a superior vertebra and an inferior vertebra, wherein the superior vertebra is displaced away from a normal anatomic position relative to the inferior vertebra so that a first side of the superior vertebra protrudes past a first side of the inferior vertebra. The method includes the steps of: providing an implant for implantation in the intervertebral space, wherein the implant includes a superior side for contacting the superior vertebra, an opposite inferior side for contacting the inferior vertebra, a first side for implantation adjacent the first sides of the superior and inferior vertebrae, and an instrument connection feature; providing an instrument including an implant connection feature and a friction-reducing feature; connecting the implant to the instrument, so that the instrument connection feature is fixed to the implant connection feature and the friction-reducing feature engages the superior side of the implant to reduce friction on the superior side of the implant; inserting the implant to a first position within the intervertebral space, while the instrument connection feature is fixed to the implant connection feature and the friction-reducing feature engages the superior side of the implant, wherein in the first position, the first side of the implant is adjacent to the first side of the superior vertebra and protrudes past the first side of the inferior vertebra; actuating the instrument to disengage the friction-reducing feature from the superior side of the implant, while the instrument connection feature remains fixed to the implant connection feature and the implant remains in the first position; inserting the implant to a second position within the intervertebral space, while the instrument connection feature remains fixed to the implant connection feature, wherein the implant and the superior vertebra move together relative to the inferior vertebra so that the superior vertebra moves toward the normal anatomic position, wherein in the second position, the first side of the implant is adjacent to the first sides of the superior and inferior vertebrae; and actuating the instrument to disconnect the instrument connection feature from the implant connection feature.

Embodiments of this aspect of the technology may include one or more of the following characteristics. Connecting the implant to the instrument leaves the inferior side of the implant exposed. When the instrument connection feature is fixed to the implant connection feature and the friction-reducing feature engages the superior side of the implant, no portion of the instrument extends over the inferior side of the implant. The friction-reducing feature includes a tab of the instrument, wherein when the tab engages the superior side of the implant, the tab protrudes superiorly above the superior side of the implant to reduce friction on the superior side of the implant. Actuating the instrument to disengage the tab from the superior side of the implant, while the instrument connection feature remains fixed to the implant connection feature and the implant remains in the first position, includes moving the tab out of the intervertebral space. The implant includes a slot extending across the superior side of the implant, wherein when the tab engages the superior side of the implant, the tab is received in the slot. Actuating the instrument to disengage the tab from the superior side of the implant includes moving the tab out of the slot.

Another aspect of the technology includes another method for spinal surgery in an intervertebral space between a superior vertebra and an inferior vertebra, wherein the superior vertebra is anteriorly displaced away from a normal anatomic position relative to the inferior vertebra so that an anterior side of the superior vertebra overhangs an anterior side of the inferior vertebra. The method includes the steps of: providing an implant for implantation in the intervertebral space, wherein the implant includes a superior side for contacting the superior vertebra, an opposite inferior side for contacting the inferior vertebra, an anterior side for implantation adjacent the anterior sides of the superior and inferior vertebrae, and an instrument connection feature; providing an instrument including an implant connection feature and a friction-reducing feature; connecting the implant to the instrument so that the instrument connection feature is fixed to the implant connection feature and the friction-reducing feature engages the superior side of the implant to reduce friction on the superior side of the implant; inserting the implant to a first position within the intervertebral space while the instrument connection feature is fixed to the implant connection feature and the friction-reducing feature engages the superior side of the implant, wherein the implant moves relative to the superior and inferior vertebrae, wherein in the first position, the anterior side of the implant is adjacent to the anterior side of the superior vertebra and overhangs the anterior side of the inferior vertebra; actuating the instrument to disengage the friction-reducing feature from the superior side of the implant while the instrument connection feature is fixed to the implant connection feature and the implant is in the first position; inserting the implant to a second position within the intervertebral space while the instrument connection feature is fixed to the implant connection feature and the friction-reducing feature is disengaged from the superior side of the implant, wherein the implant and the superior vertebra move together relative to the inferior vertebra so that the superior vertebra moves toward the normal anatomic position, wherein in the second position, the anterior side of the implant is adjacent to the anterior sides of the superior and inferior vertebrae; and actuating the instrument to disconnect the instrument connection feature from the implant connection feature.

Embodiments of this aspect of the technology may include one or more of the following characteristics. Connecting the implant to the instrument includes leaving the inferior side of the implant exposed. When the instrument connection feature is fixed to the implant connection feature and the friction-reducing feature engages the superior side of the implant, no portion of the instrument extends over the inferior side of the implant. The friction-reducing feature includes a tab of the instrument, wherein when the tab engages the superior side of the implant, the tab extends across the superior side of the implant and protrudes superiorly beyond the superior side of the implant to reduce friction on the superior side of the implant. Actuating the instrument to disengage the tab from the superior side of the implant includes moving the tab out of the intervertebral space while the implant is in the first position. The implant includes a slot extending across the superior side of the implant, wherein when the tab engages the superior side of the implant, the tab is received in the slot. Actuating the instrument to disengage the tab from the superior side of the implant includes moving the tab out of the slot.

In another aspect of the technology, a system for spinal surgery in an intervertebral space between a superior vertebra and an inferior vertebra includes: an implant for implantation in the intervertebral space, wherein the implant includes a superior side for contacting the superior vertebra, an opposite inferior side for contacting the inferior vertebra, and an instrument connection feature; and an instrument including an implant connection feature and a friction-reducing feature, wherein the instrument is connectable to the implant, wherein the instrument includes first, second, and third states; wherein in the first state, the implant connection feature is in an unlocked state and the friction-reducing feature is in a disengaged state, wherein in the unlocked state, the implant connection feature is not fixed to the instrument connection feature, wherein when the instrument is connected to the implant and the friction-reducing feature is in the disengaged state, the friction-reducing feature is spaced apart from the implant so that no portion of the instrument extends over the superior side of the implant; wherein in the second state, the implant connection feature is in a locked state and the friction-reducing feature is in an engaged state, wherein when the instrument is connected to the implant and the implant connection feature is in the locked state, the implant connection feature is fixed to the instrument connection feature, wherein when the instrument is connected to the implant and the friction-reducing feature is in the engaged state, the friction-reducing feature engages the superior side of the implant; wherein in the third state, the implant connection feature is in the locked state and the friction-reducing feature is in the disengaged state.

Embodiments of this aspect of the technology may include one or more of the following characteristics. When the instrument is connected to the implant, no portion of the instrument extends over the inferior side of the implant. When the instrument is connected to the implant and the instrument is in the second state, no portion of the instrument extends over the inferior side of the implant. The friction-reducing feature is a tab of the instrument, wherein when the instrument is connected to the implant and the tab is in the engaged state, the tab protrudes superiorly beyond the superior side of the implant to reduce friction on the superior side of the implant. The implant includes a slot extending across the superior side of the implant, when the instrument is connected to the implant and the tab is in the engaged state, the tab is received in the slot. When the instrument goes between the second and third states, the tab slides relative to the slot.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 12 is an oblique partially-exploded view of the intervertebral cage and inserter instrument of FIG. 10, from a generally posterior direction;

FIG. 13 is another oblique partially-exploded view of the intervertebral cage and inserter instrument of FIG. 10, from a generally inferior-lateral direction;

DETAILED DESCRIPTION

Figure 1:
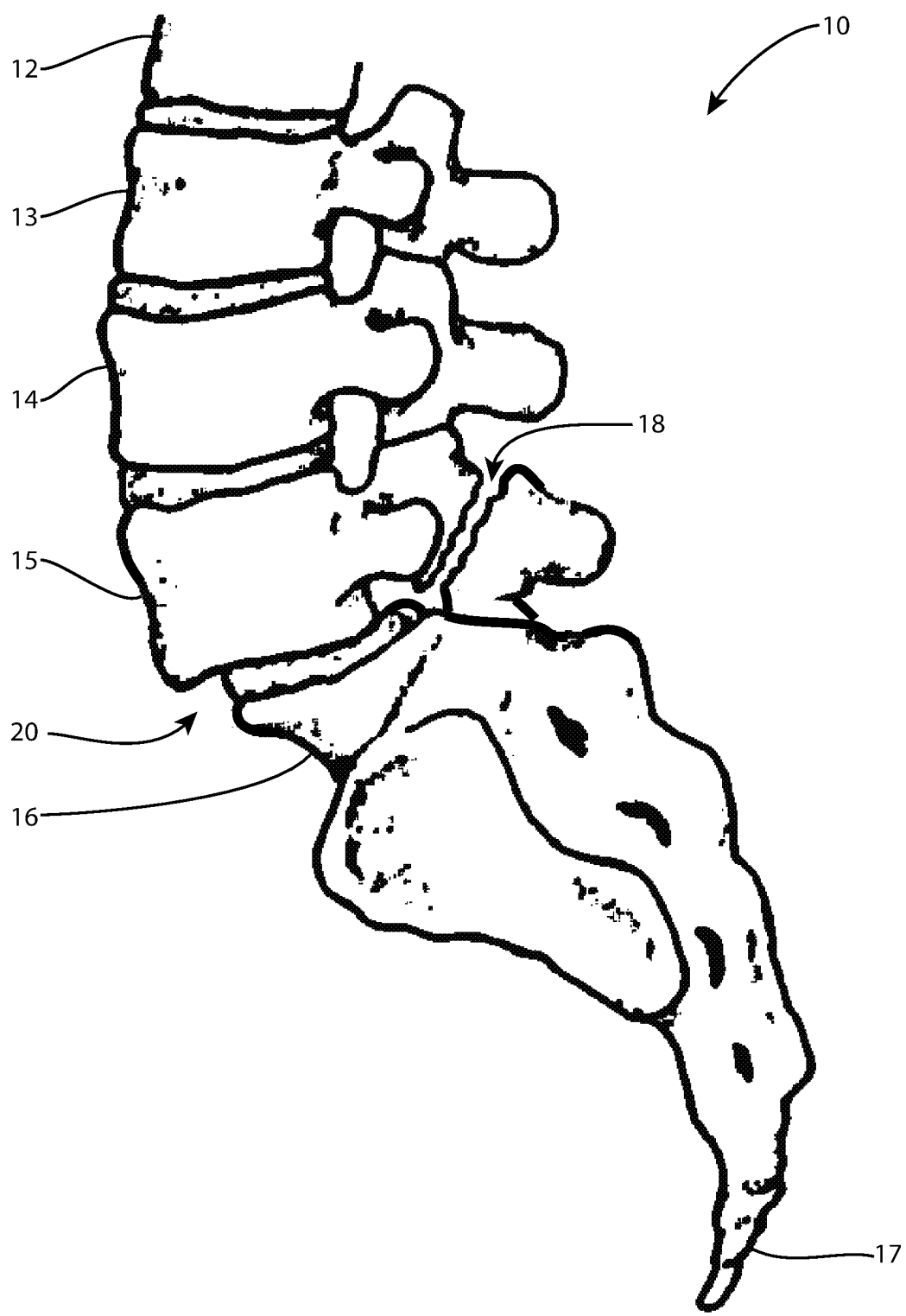
FIG. 1 is a lateral view of a sacrum and lumbar vertebrae.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance. Aspect means that part of a surface or structure viewed from a particular direction: an anterior aspect of a vertebra includes the surfaces of the vertebra visible from an anterior direction.

In this specification, standard spinal directional and anatomical terms are employed with their ordinary and customary meanings.

Referring to FIG. 1, an inferior portion of a spine 10 is illustrated, including an inferior portion of a lumbar vertebra L2 12, a lumbar vertebra L3 13, a lumbar vertebra L4 14, a lumbar vertebra L5 15, a sacrum 16, and a coccyx 17. Lumbar vertebra L5 15 is anteriorly displaced relative to the sacrum 16. A fracture 18 of the pars interarticularis of L5 15 is shown. FIG. 1 illustrates spondylolisthesis 20 between L5 15 and the sacrum 16, in other words at spinal level L5/S1.

Figure 2:
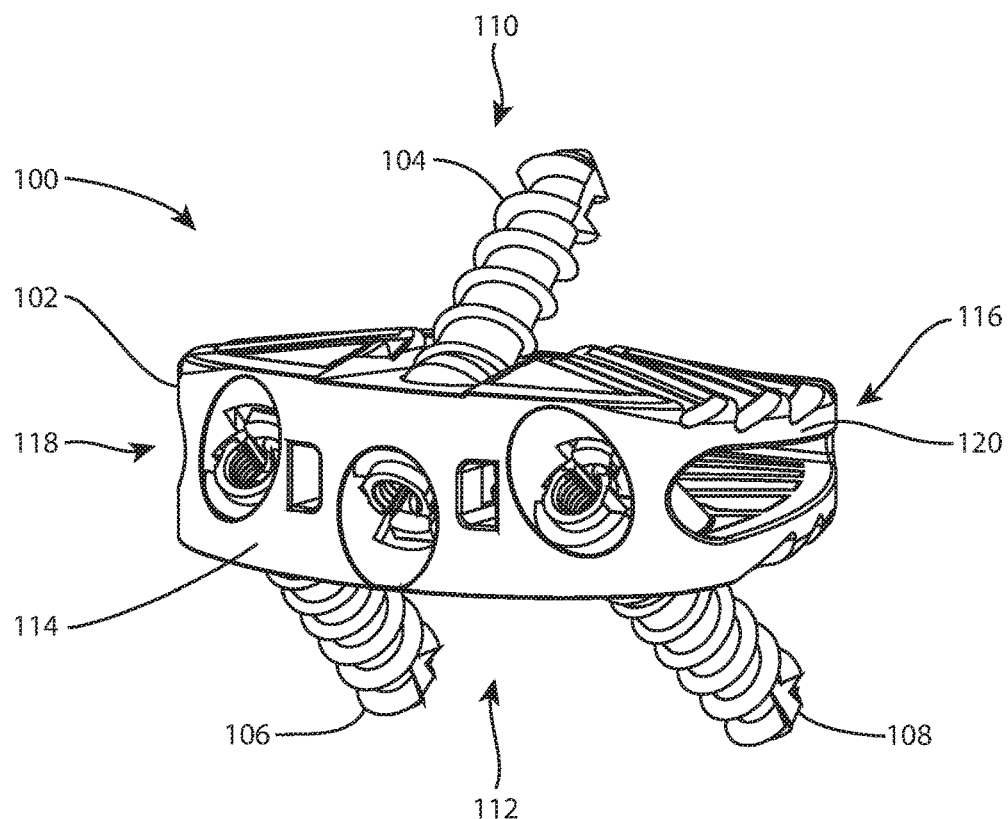
FIG. 2 is an oblique view of an implant assembly, showing superior, anterior, and left sides of the implant assembly.
Figure 3:
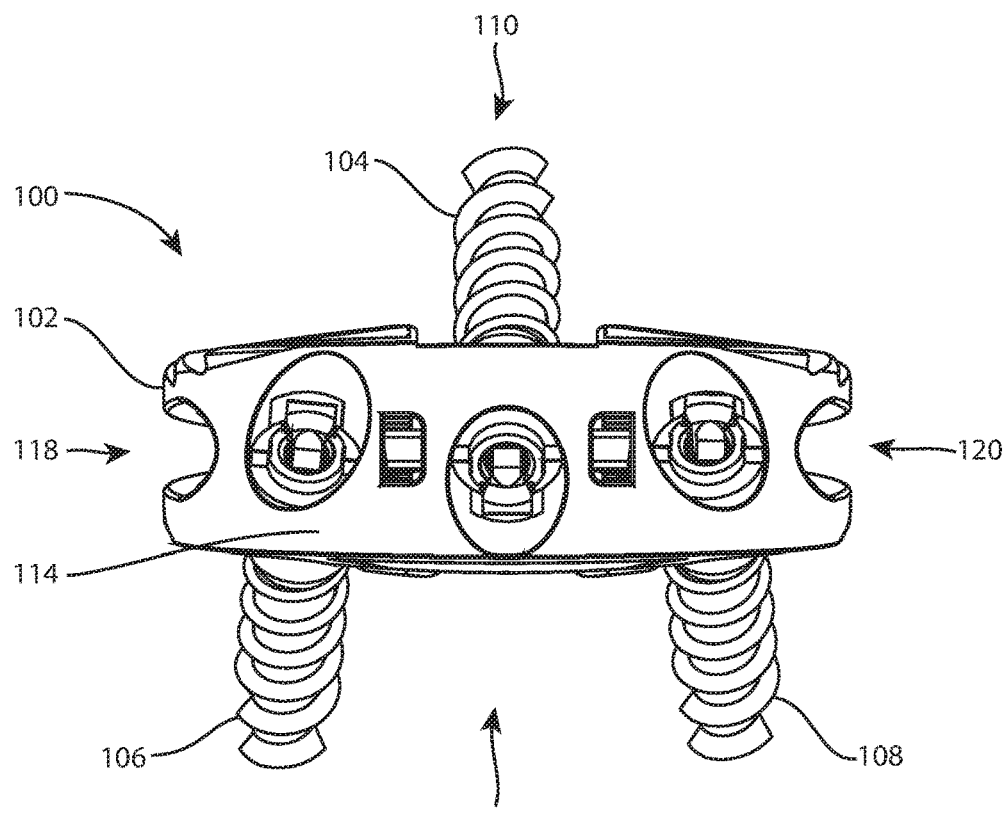
FIG. 3 is an anterior view of the implant assembly of FIG. 2.

Referring to FIGS. 2-3, an implant assembly 100 includes an intervertebral spacer 102. The implant assembly 100 may include one or more fixation elements, such as a bone screw 104. Three bone screws 104, 106, 108 are shown. The implant assembly 100 may include a plate (not shown). The illustrated implant assembly 100 is adapted for an anterior approach to the spine, so that the assembly, and each of its component parts, has a superior side 110 for contacting a superior vertebra, an inferior side 112 for contacting an inferior vertebra, an anterior side 114, a posterior side 116, a right side 118, and a left side 120. However, the implant assembly 100 may be adapted for other approaches to the spine: lateral, posterior, or oblique (antero-lateral, postero-lateral) approaches. Therefore, more generally, the superior side 110 may be referred to as a first bone-facing side, the inferior side 112 may be referred to as a second bone-facing side, the anterior side 114 may be referred to as a trailing side, the posterior side 116 may be referred to as a leading side, the right side 118 may be referred to as a first lateral side, and the left side 120 may be referred to as a second lateral side.

Figure 4:
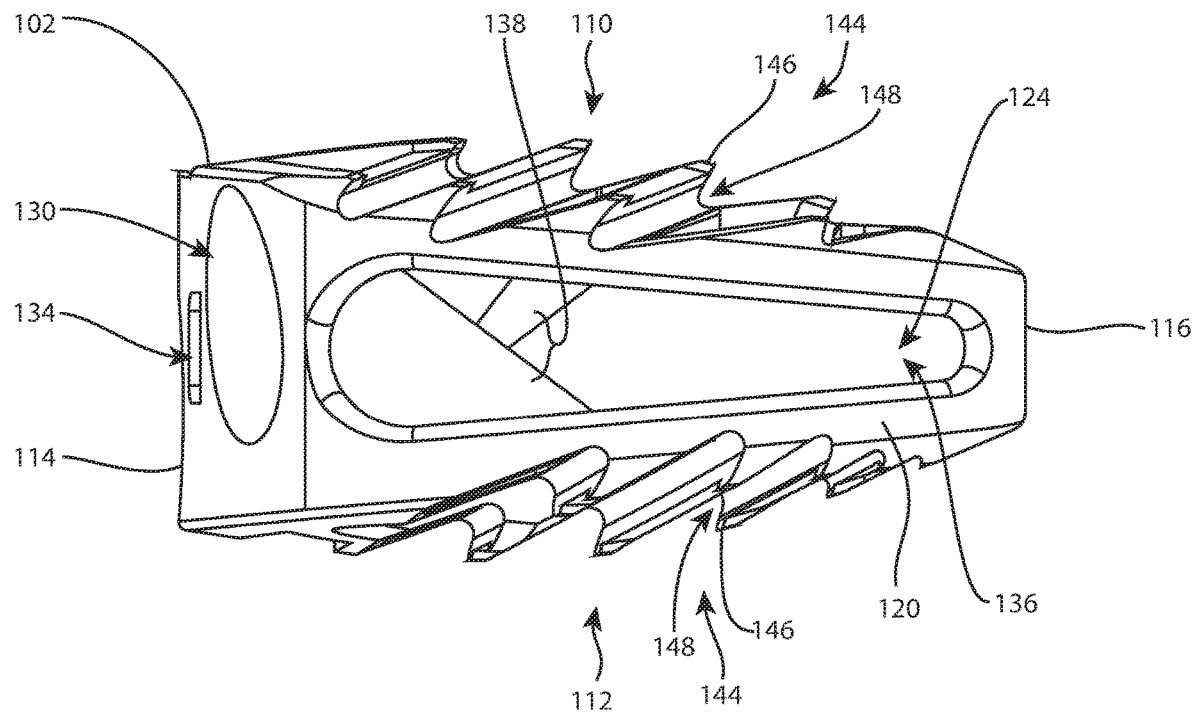
FIG. 4 is a lateral view of an intervertebral cage of the implant assembly of FIG. 2 showing the left side of the intervertebral cage.
Figure 8:
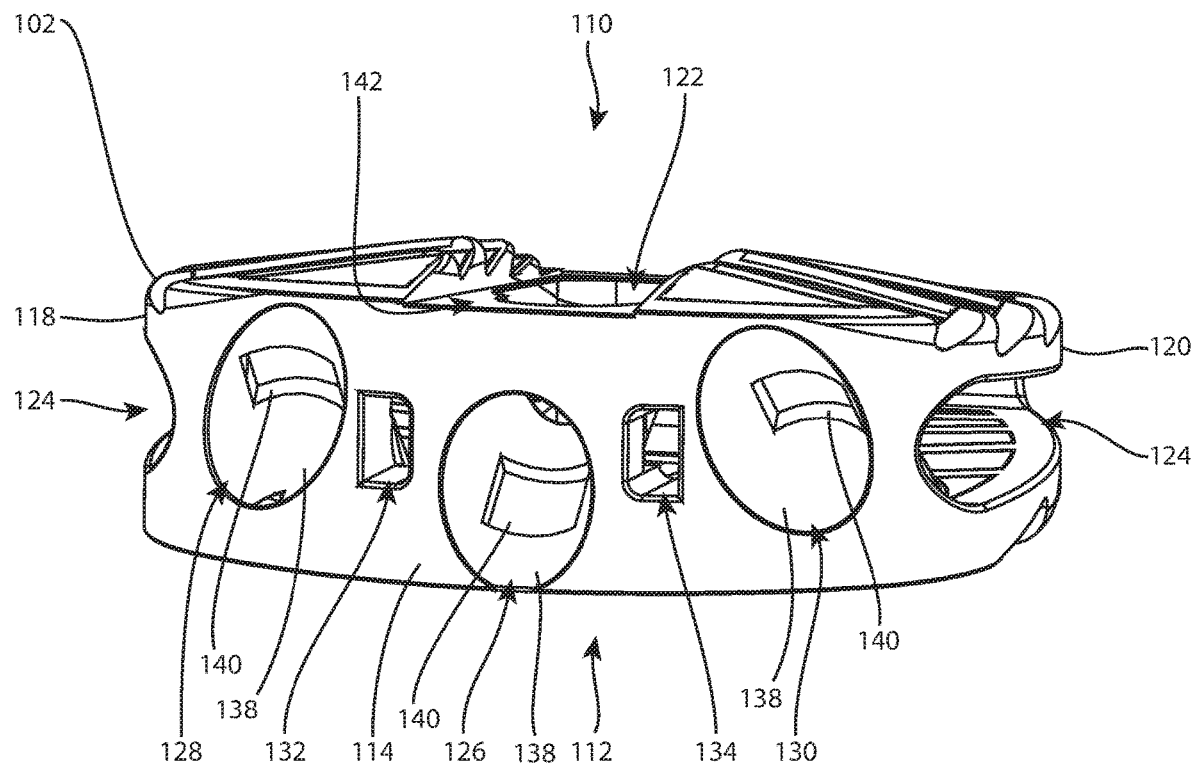
FIG. 8 is yet another oblique view of the intervertebral cage of FIG. 4, showing superior, anterior, and left sides of the intervertebral cage.

Referring to FIGS. 4-8, the spacer 102 may be referred to as a fusion cage or, more generally, as an implant. The superior side 110 of the spacer 102 may be convex in one or more views. As seen best in FIGS. 4 and 8, the superior side 110 is shown convex in a lateral view (FIG. 4) and in an anterior view (FIG. 8). FIG. 4 illustrates that the superior side 110 may taper from the anterior side 114 to the posterior side 116, so that the superior-inferior height of the spacer 102 is greater anteriorly than it is posteriorly to provide a lordotic correction angle. Similarly, the inferior side 112 of the spacer 102 may be convex in one or more views, and/or tapered from anterior to posterior. Alternatively, the superior and inferior sides 110, 112 of the spacer 102 may be flat or planar, convex, or another shape suited to a particular approach to the spine and/or spinal level. Likewise, the superior and inferior sides 110, 112 of the spacer 102 may taper along a different direction suited to a particular approach to the spine, spinal level, or desired lordotic/kyphotic/scoliotic correction angle, or they may be parallel to each other.

The spacer 102 may include one or more holes, fenestrations, windows, or apertures. The illustrated spacer 102 includes seven holes. The spacer embodiment shown in FIGS. 2, 3, and 8 illustrates a first arrangement of holes. The spacer embodiment shown in FIGS. 4-7 illustrates a second arrangement of holes. The two embodiments differ in the orientation of the fourth hole, discussed below. The two embodiments may be the same in all other respects.

A first hole 122 extends through the spacer 102 between the superior and inferior sides 110, 112. The first hole 122 may be centrally located between the right and left sides 118, 120. In a superior or inferior view, the first hole 122 may be D-shaped, with a rounded anterior portion and a flat posterior portion. The first hole 122 may receive bone graft, so that the graft may contact the adjacent vertebral endplates to eventually fuse the vertebrae together. A second hole 124 extends through the spacer 102 between the right and left sides 118, 120. The second hole 124 may be centrally located between the superior and inferior sides 110, 112. In a right or left lateral view, the second hole 124 may be an oval, with rounded anterior and posterior portions. The second hole 124 may taper from anterior to posterior as shown, so that the superior-inferior height is greater anteriorly than it is posteriorly. The second hole 124 may provide a window through the spacer 102 so that the bone graft and developing fusion mass may be seen radiographically. A third hole 126 extends through the spacer 102 between the anterior and superior sides 114, 110. The third hole 126 may be centrally located between the right and left sides 118, 120.

FIGS. 2, 3, and 8 show an embodiment with a fourth hole 128 that extends through the spacer 102 between the anterior and inferior sides 114, 112. FIGS. 4-7 show an embodiment with a fourth hole 129 that extends through the spacer 102 between the anterior and superior sides 114, 110. In both embodiments, the fourth hole 128 or 129 may be located between the third hole 126 and the right side 118, so that the fourth hole 128 or 129 may be referred to as a right hole.

A fifth hole 130 extends through the spacer 102 between the anterior and inferior sides 114, 112. The fifth hole 130 may be located between the third hole 126 and the left side 120, so that the fifth hole 130 may be referred to as a left hole. The third, fourth, and fifth holes 126, 128, 130 may be circular, and may receive fasteners such as the bone screws 104, 106, 108. The third, fourth, and fifth holes 126, 128, 130 may be angled and/or oriented to position the fasteners as desired for a particular approach to the spine, treated spinal level, or treatment modality. A sixth hole 132 extends through the anterior side 114 of the spacer 102. The sixth hole 132 may be located between the third hole 126 and the fourth hole 128. A seventh hole 134 extends through the anterior side 114 of the spacer 102. The seventh hole 134 is located between the third hole 126 and the fifth hole 130. The sixth and seventh holes 132, 134 may be D-shaped as shown, and may receive portions of an instrument, as discussed below. The sixth and seventh holes 132, 134 may be referred to as inserter instrument connection features.

The holes 122, 124, 126, 132, and 134 may intersect within the spacer 102 to form an interior cavity 136 or internal chamber, which may be centrally located within the spacer. The holes 122, 124, 126, 132, and 134 may be said to communicate with the cavity 136. The cavity 136 may receive bone graft for eventual development of a fusion mass between the adjacent vertebrae.

Each hole 128, 129, and 130 may be surrounded by a wall 138 which separates the hole from the cavity 136. The hole 126 may also be said to have a wall 138, although hole 126 may communicate with the cavity.

As shown best in FIG. 8, each hole 126, 128, 130 may include a fastener locking feature 140 which locks a fastener to the spacer 102 when the fastener is fully seated within the hole.

A slot 142 or groove or notch may extend across the superior side 110 of the spacer 102 along an anterior-posterior direction. The slot 142 may extend through the anterior side 114 of the spacer 102 and continue posteriorly across some or all of the superior side 110. The slot 142 may or may not extend through the posterior side 116 of the spacer 102. The slot 142 may receive a portion of an instrument, as discussed below. The slot 142 may be referred to as an insertion tool guide feature.

Serrations 144 may be present on the superior and/or inferior sides 110, 112 of the spacer 102. The serrations 144 may include alternating teeth 146 and grooves 148. The serrations 144 may extend between the right and left sides 118, 120 of the spacer 102, as shown, or, more generally, transverse to the approach to the spine. Four serrations 144 are shown on each of the superior and inferior sides 110, 112 in FIG. 4, although any number of serrations may be present. The superior serrations 144 are angled so that the teeth 146 point superiorly and posteriorly. The inferior serrations 144 are angled so that the teeth 146 point inferiorly and anteriorly. Referring briefly to FIG. 1, the superior teeth 146 are angled to grip the L5 vertebra 15 and push it posteriorly, while the inferior teeth 146 are angled to grip the sacrum 16 to resist any tendency for the L5 vertebra 15 to slip anteriorly again, or for the spacer 102 to slip out anteriorly. However, the inferior teeth 146 are angled so that they present minimal resistance against the sacral endplate when the spacer 102 is inserted into an intervertebral space from anterior to posterior. The superior and inferior teeth may be angled differently as appropriate for different approaches to the spine, different spinal levels, and/or different treatment modalities.

Each serration 144 (tooth 146 and groove 148) is depicted with an adjacent aperture 150 that extends through the superior or inferior side 110, 112 of the spacer 102. The apertures 150 may be filled by bone ingrowth/ongrowth structure, such as porous structure, rather than being empty as shown. Other recessed areas of the superior or inferior sides 110, 112 of the spacer 102 may also be filled by bone ingrowth/ongrowth structure. The bone ingrowth/ongrowth structure may be fabricated simultaneously with solid portions of the spacer 102 by a process such as additive manufacturing, or the bone ingrowth/ongrowth structure may be fabricated separately and attached to solid portions of the spacer 102 by a process such as sintering.

The spacer 102 may include alternate directional high friction surface treatments, features, or structures on the superior and/or inferior sides 110, 112, instead of the illustrated serrations 144. For example, barbs, teeth, spikes, ridges, blades, knurling, and the like may be present. The high friction elements on the superior side 110 may be oriented to provide high friction against a corresponding superior vertebra to resist any tendency of the superior vertebra to move anteriorly relative to the spacer 102, and low friction for posterior movement of the superior vertebra relative to the spacer. The high friction elements on the inferior side 112 may be oriented to provide high friction against a corresponding inferior vertebra to resist any tendency of the spacer 102 to move anteriorly relative to the inferior vertebra, and low friction for posterior movement of the spacer relative to the inferior vertebra. It will be appreciated that the high friction elements may be oriented in other directions, depending upon the planned surgical approach to the spine and direction of relative vertebral displacement.

Figure 9:
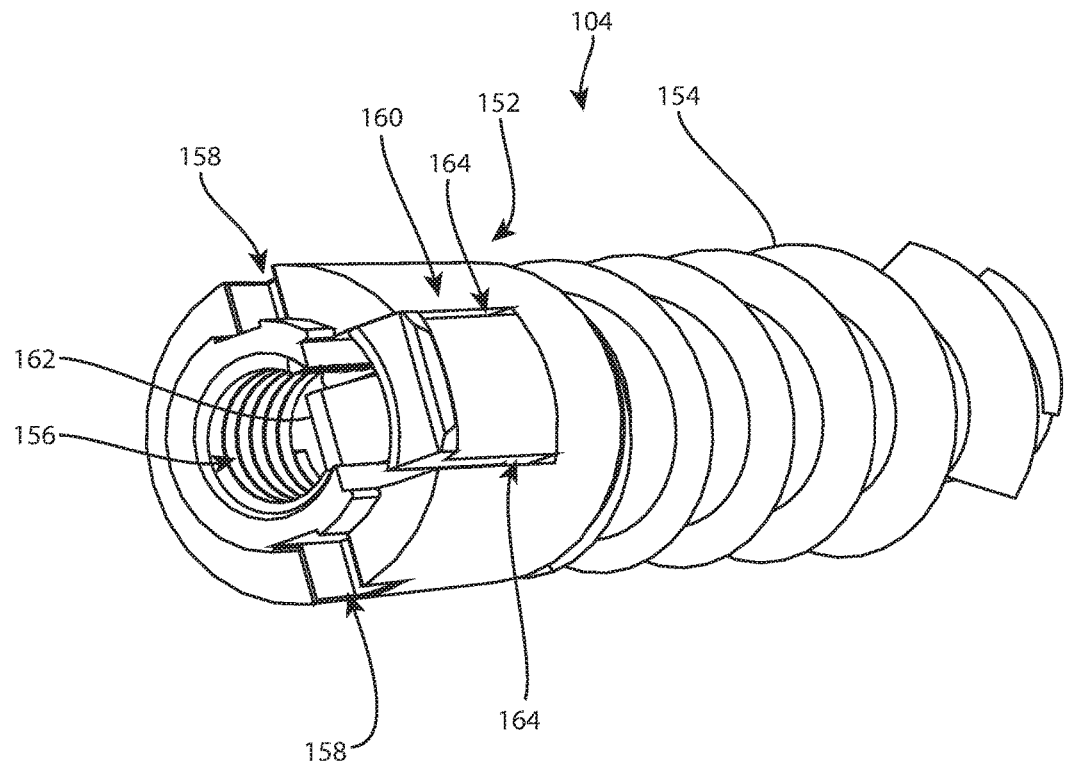
FIG. 9 is an oblique view of a bone screw of the implant assembly of FIG. 2.

Referring to FIG. 9, the bone screw 104 may include a head 152 and an externally threaded shaft 154 that extends from the head. The head 152 may include an internally threaded socket 156 that receives an externally threaded tip of a screwdriver (not shown), bilateral notches 158 that receive corresponding tabs of the screwdriver for torque transmission, and a spacer locking feature 160, which in this example is a resilient tab 162 flanked by bilateral slits 164. The spacer locking feature 160 may engage the fastener locking feature 140 when the bone screw 104 is fully engaged in a hole 126, 128, 129, or 130 of the spacer 102. The bone screws 106, 108 may be identical to the bone screw 104.

The implant assembly 100 may be assembled by inserting bone screw 104 in spacer hole 126, inserting bone screw 106 in spacer hole 128 or 129, and inserting bone screw 108 in spacer hole 130. The bone screw 104 may be referred to as a superior bone screw, the bone screw 106 may be referred to as an inferior right bone screw, and the bone screw 108 may be referred to as an inferior left bone screw.

When the implant assembly 100 is assembled, the heads 152 of the bone screws 104, 106, 108 are received in the corresponding spacer holes 126, 128 or 129, and 130, and the screw shafts 154 extend outwardly from the spacer 102 to engage the adjacent vertebrae to secure the implant assembly 100 to the vertebrae. The heads 152 may be locked in the spacer holes 126, 128 or 129, and 130 due to engagement between the fastener locking features 140 and the spacer locking features 160.

Figure 10:
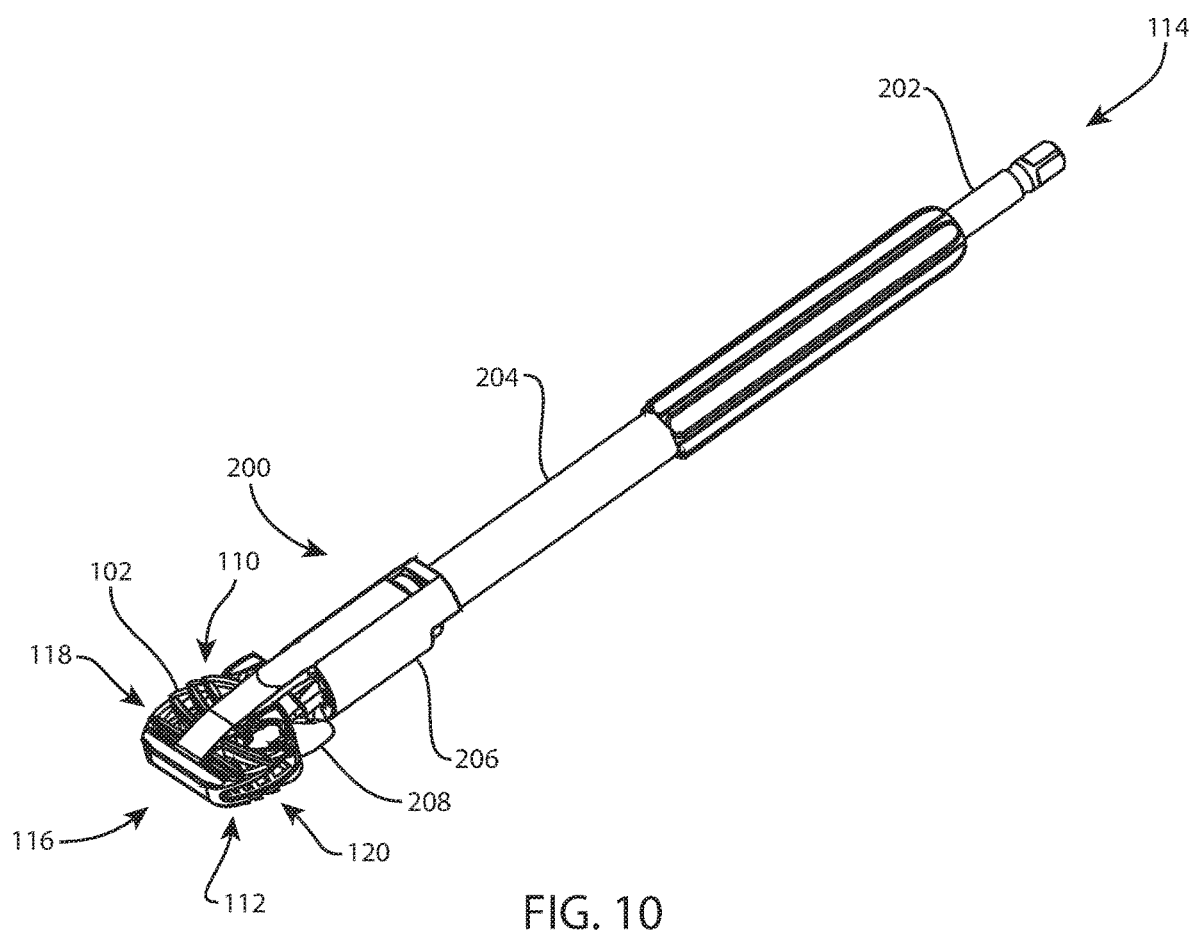
FIG. 10 is an oblique view of the intervertebral cage of FIG. 4 connected to an inserter instrument.
Figure 11:
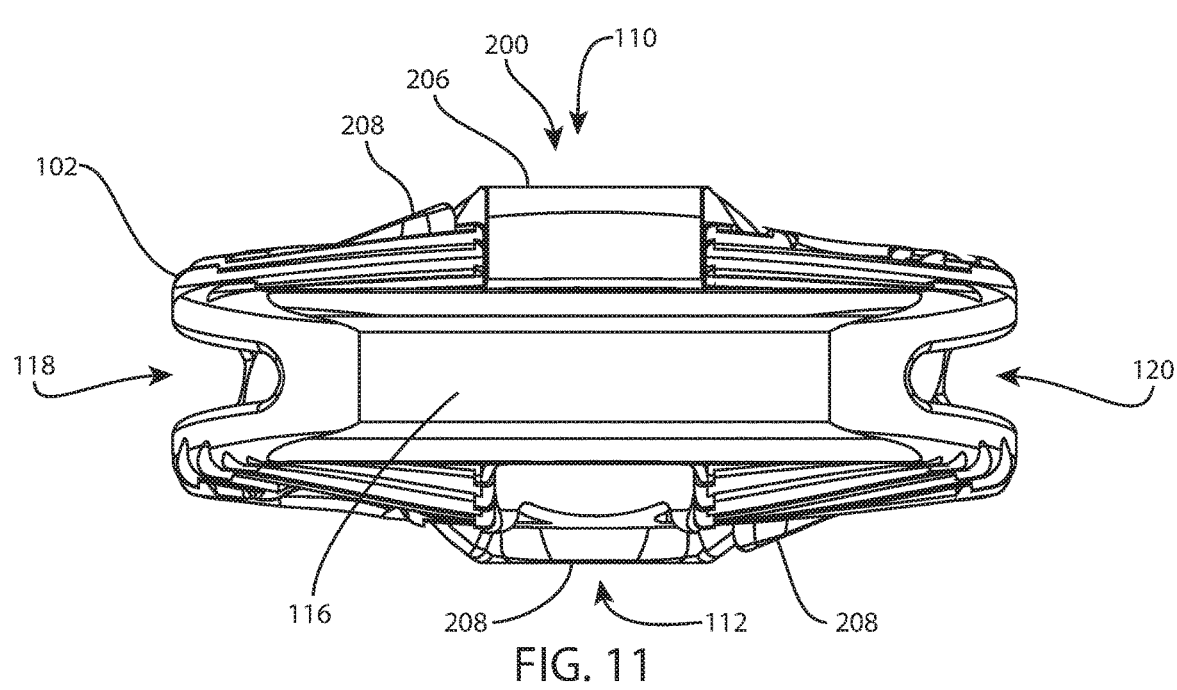
FIG. 11 is a posterior view of the intervertebral cage and inserter instrument of FIG. 10.
Figure 14:
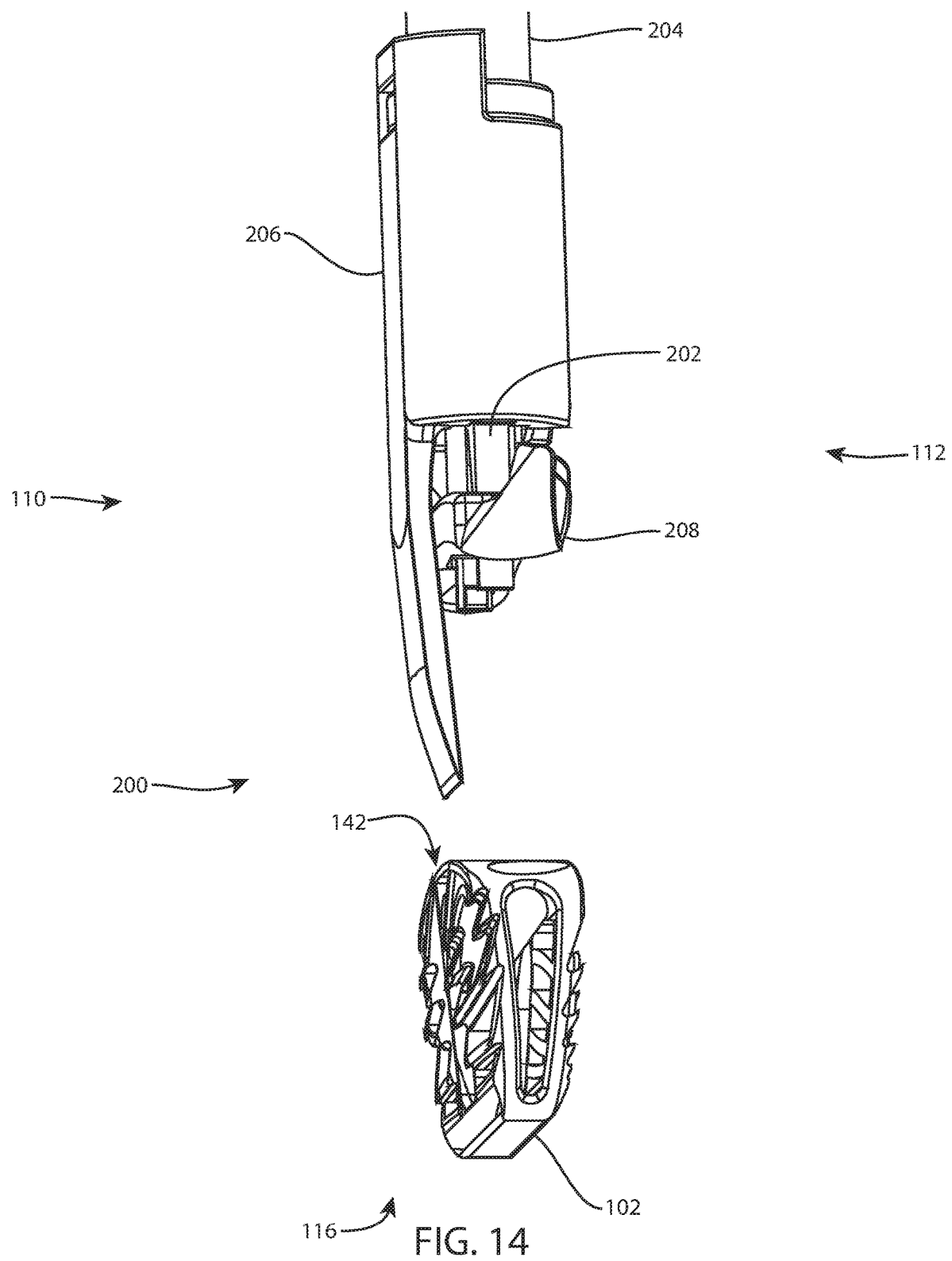
FIG. 14 is yet another oblique partially-exploded view of the intervertebral cage and inserter instrument of FIG. 10, from a generally superior-lateral direction.

Referring to FIGS. 10-11, the spacer 102 is shown connected to an inserter instrument 200. The inserter instrument 200 may include a shaft 202, a sleeve 204, a wedge 206, and a drill guide 208. The illustrated spacer 102 and inserter instrument 200 are adapted for an anterior approach to the spine, so that the inserter instrument 200, and each of its component parts, has a superior side 110, an inferior side 112, an anterior side 114, a posterior side 116, a right side 118, and a left side 120. However, the spacer 102 and inserter instrument 200 may be adapted for other approaches to the spine: lateral, posterior, or oblique (antero-lateral, postero-lateral) approaches. Therefore, more generally, the superior side 110 may be referred to as a first bone-facing side, the inferior side 112 may be referred to as a second bone-facing side, the anterior side 114 may be referred to as a trailing side, the posterior side 116 may be referred to as a leading side, the right side 118 may be referred to as a first lateral side, and the left side 120 may be referred to as a second lateral side. Alternatively, the anterior side 114 may be referred to as a proximal side (relatively closer to a user) and the posterior side 116 may be referred to as a distal side (relatively farther from a user).

Figure 15:
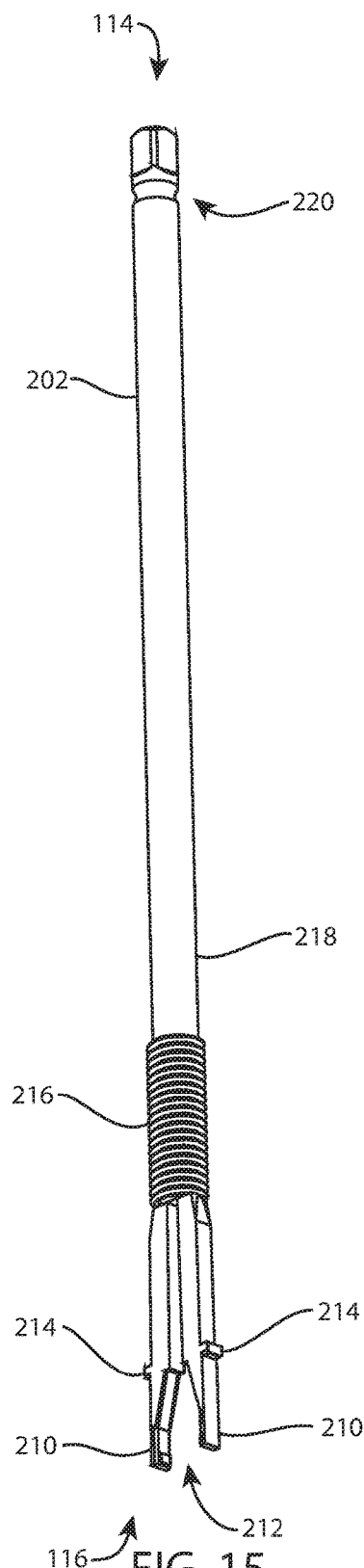
FIG. 15 is an oblique view of a shaft of the inserter instrument of FIG. 10.

Referring to FIG. 15, the shaft 202 may have a pair of jaws 210 separated by a notch 212. The jaws 210 may be referred to as implant connection features. The most posterior portions of the jaws 210 may extend inwardly toward each other. A tab 214 may protrude from an outer surface of each jaw 210 opposite the notch 212 and spaced apart from the posterior tip of the shaft 202. The shaft 202 may include an externally threaded portion 216 that extends anteriorly from the anterior end of the jaws 210 and notch 212. A smooth portion 218 may extend anteriorly from the anterior end of the threaded portion 216. A torque fitting 220 or quick connect may be present at the anterior tip of the shaft 202. The fitting 220 may couple to a T-handle, drill, or other item (not shown).

Figure 16:
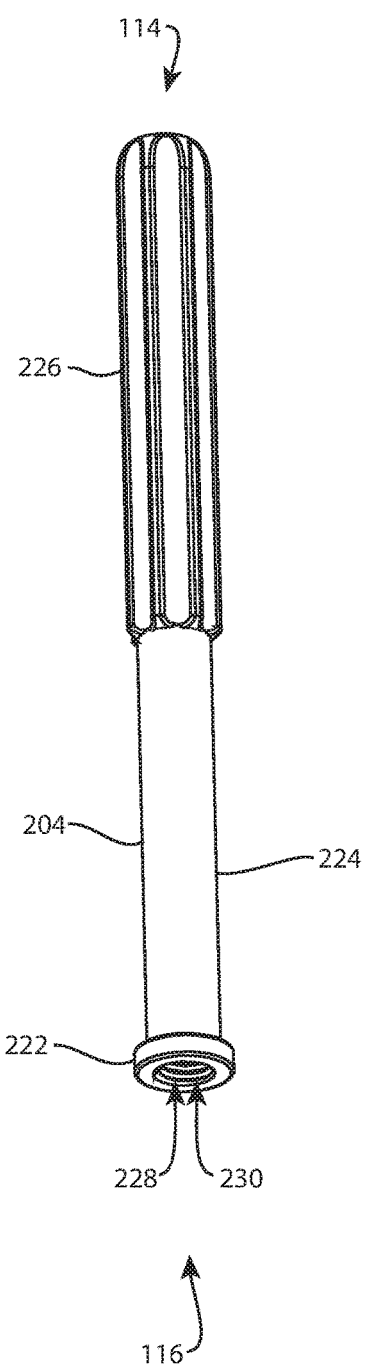
FIG. 16 is an oblique view of a sleeve of the inserter instrument of FIG. 10.
Figure 17:
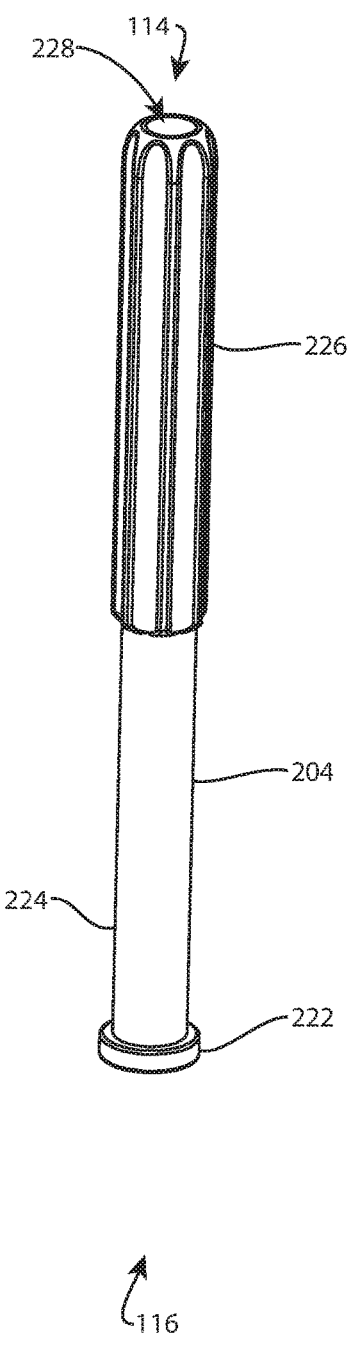
FIG. 17 is another oblique view of the sleeve of FIG. 16, from a different direction.

Referring to FIGS. 16-17, the sleeve 204 may include a flange 222 at the posterior end, a smooth shaft portion 224 anterior to the flange 222, and a longitudinally fluted portion 226 at the anterior end. The sleeve 204 may include a longitudinal through hole 228 with an internally threaded portion 230 extending into the posterior end of the sleeve 204.

Figure 18:
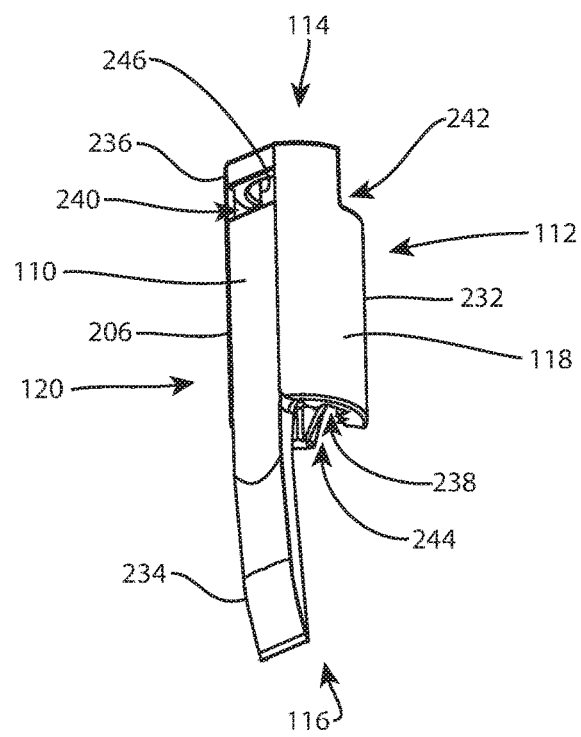
FIG. 18 is an oblique view of a wedge of the inserter instrument of FIG. 10.
Figure 19:
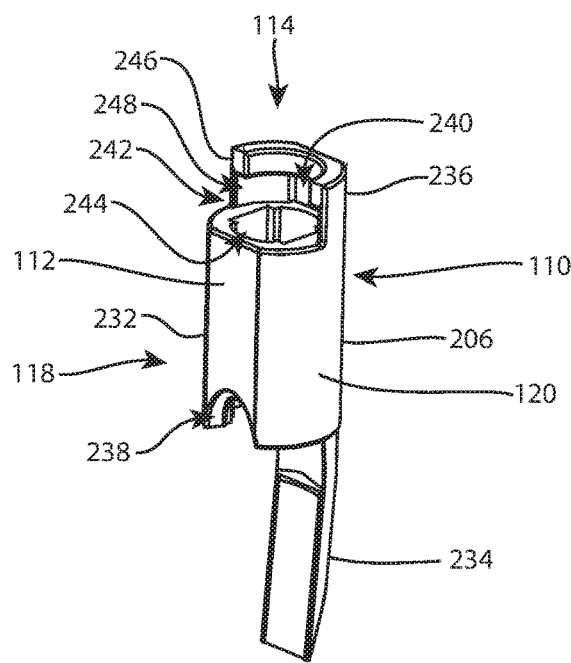
FIG. 19 is another oblique view of the wedge of FIG. 18, from a different direction.

Referring to FIGS. 18-19, the wedge 206 may include a body 232 with a unilateral tab 234 that extends posteriorly from the superior side 110 of the body 232 and a unilateral semicircular wall 236 that extends anteriorly from the superior side 110 of the body 232. A notch 238 may be opposite the tab 234 and may extend anteriorly through the inferior side 112 of the body 232. The notch 238 may have a rounded anterior side as shown. A hole 240 may extend transversely through the wall 236. The hole 240 may be rectangular as shown. A notch 242 may be opposite the wall 236 at the anterior end of the body 232. The notch 242 may form a 90 degree internal corner as shown. The superior 110 and inferior 112 sides of the body 232 may be flat. A hole 244 may extend longitudinally through the wedge 206 along an anterior-posterior direction. The hole 244 may have a non-circular cross-sectional profile, as seen best in FIG. 19. A semicircular shelf 246 may be formed around the interior concave side of the wall 236 at its anterior end. An undercut 248 may exist between the posterior side of the shelf 246 and the anterior side of the notch 242.

Figure 20:
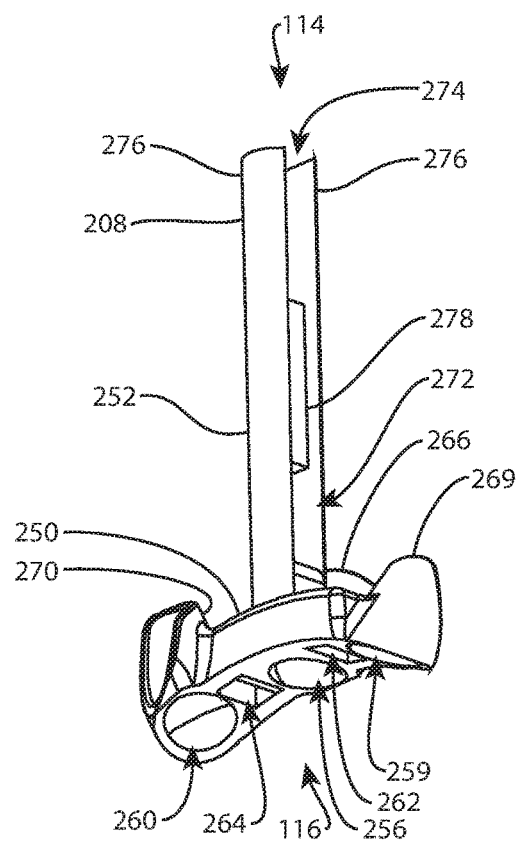
FIG. 20 is an oblique view of a drill guide of the inserter instrument of FIG. 10.
Figure 21:
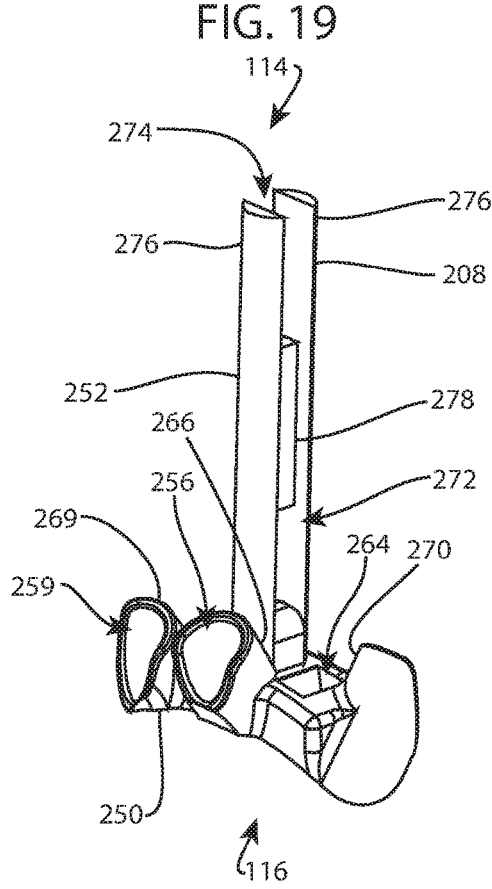
FIG. 21 is another oblique view of the drill guide of FIG. 20, from a different direction.

Referring to FIGS. 20-21, the drill guide 208 may include a posterior body 250 and a shaft 252 that extends anteriorly from the body 250. The body 250 may be elongated along a right-left direction. The body 250 may include one or more holes corresponding to the fastener holes of the spacer 102. The illustrated body 250 includes holes 256, 259, 260 that correspond to the holes 126, 129, 130 of the spacer 102 shown in FIGS. 4-7, respectively. The hole 256 extends through a barrel 266, the hole 259 extends through a barrel 269, and the hole 260 extends through a barrel 270. In an alternate embodiment of the drill guide, the hole 259 and barrel 269 may be re-oriented to correspond to hole 128 of the spacer 102 shown in FIGS. 2, 3, and 8. The body 250 may include holes 262, 264 corresponding to the instrument holes 132, 134 of the spacer 102, respectively. The shaft 252 may have a circular outer cross-sectional profile. A window 272 may extend through the shaft 252 just anterior to the body 250. The window 272 may be rectangular as shown. A notch 274 may extend posteriorly into the anterior end of the shaft 252, splitting the anterior end of the shaft into two prongs 276. A web 278 may extend between the anterior end of the window 272 and the posterior end of the notch 274.

The inserter instrument 200 may be assembled by performing some or all of the following steps in any order: inserting the flange 222 of the sleeve 204 into the undercut 248 of the wedge 206, as best seen in FIG. 10; inserting the smooth portion 218 of the shaft 202 through the hole 244 of the wedge 206 and the hole 228 of the sleeve 204 from posterior to anterior; threading the externally threaded portion 216 of the shaft 202 into the internally threaded portion 230 of the sleeve 204 so that the jaws 210 are next to the tab 234, as best seen in FIG. 13; and sliding the shaft 252 of the drill guide 208 into the hole 244 of the wedge 206 from posterior to anterior so that the web 278 is received in the notch 212 of the shaft 202 and the jaws 210 are received in the holes 262, 264. The inserter instrument 200 may be disassembled by reversing the assembly steps.

When the inserter instrument 200 is assembled, the sleeve 204 may be rotated clockwise and counterclockwise relative to the shaft 202 to move the sleeve 204 and wedge 206 axially (longitudinally) relative to the shaft 202 by virtue of the threaded interconnection between the sleeve 204 and shaft 202 and the flange 222/undercut 248 interconnection between the sleeve 204 and the wedge 206. The shaft 202, the drill guide 208, and the wedge 206 may be fixed relative to each other in rotation, i.e., unable to rotate relative to each other.

The inserter instrument 200 may have a fully retracted state, in which the sleeve 204 and wedge 206 are located as far anterior as possible relative to the shaft 202 while maintaining threaded engagement between the externally threaded portion 216 of the shaft 202 and the internally threaded portion 230 of the sleeve 204. As the sleeve 204 and wedge 206 move anteriorly relative to the shaft 202, the jaws 210 may open sufficiently to enter or exit the holes 132, 134 of the spacer 102. In one example, the jaws 210 may open up only after the tab 234 of the wedge 206 moves far enough anteriorly to be completely out of the slot 142 of the spacer 102. When the jaws 210 are open, the drill guide 208 may be free to slide axially relative to the shaft 202 and the wedge 206. The fully retracted state may be referred to as an unlocked state or open state. In the fully retracted state, the jaws 210 are in an unlocked or open state, not fixed to the holes 132, 134 of the spacer 102; and the tab 234 is in a disengaged state, positioned so far anteriorly that even when the jaws 210 are inserted into the holes 132, 134, no portion of the inserter instrument 200 extends over the superior side 110 of the spacer 102.

The inserter instrument 200 may have a fully extended state, in which the sleeve 204 and wedge 206 are located as far posterior as possible relative to the shaft 202 while maintaining threaded engagement between the externally threaded portion 216 of the shaft 202 and the internally threaded portion 230 of the sleeve 204. The tabs 214 of the shaft 202 may be received in the hole 244 of the wedge 206. As the sleeve 204 and wedge 206 move posteriorly relative to the shaft 202, the jaws 210 may close together sufficiently to clamp or fixate within the holes 132, 134 of the spacer 102. When the jaws 210 are closed, the web 278 of the drill guide 208 may be pinched or fixed within the notch 212 of the shaft. Furthermore, in the fully extended state, the tab 234 of the wedge 206 may be located far enough posteriorly to fully engage the slot 142 of the spacer 102. The fully extended state may be referred to as a locked state or a closed state or an initial spacer insertion state. In the fully extended state, the jaws 210 are in a locked or closed state and the tab 234 is in an engaged state. When the inserter instrument 200 is connected to the spacer 102 in the fully extended state, the jaws 210 are fixed to the holes 132, 134, the tab 234 is in the slot 142, and the tab 234 protrudes superiorly past the superior side 110 of the spacer 102.

The inserter instrument 200 may have an intermediate state, in which the sleeve 204 and wedge 206 are located somewhere between the farthest anterior and farthest posterior positions. In the intermediate state, the tab 234 of the wedge 206 may be located far enough anteriorly to be completely out of the slot 142 of the spacer 102, yet the jaws 210 remain closed sufficiently to clamp within the holes 132, 134 of the spacer 102. The intermediate state may be referred to as a secondary spacer insertion state. When the inserter instrument 200 is connected to the spacer 102 in the intermediate state, the jaws are fixed to the holes 132, 134 and no portion of the inserter instrument 200 extends over the superior side 110 of the spacer 102.

The inserter instrument 200 may be connected to the spacer 102 by placing the inserter instrument 200 in the fully retracted state, inserting the jaws 210 of the shaft 202 into the holes 132, 134 of the spacer 102 from anterior to posterior, and actuating the inserter instrument 200 to move the inserter instrument from the fully retracted state toward the fully extended state so that the jaws 210 clamp within the holes 132, 134 of the spacer 102 to fix the inserter instrument 200 and the spacer 102 together and so that the tab 234 of the wedge 206 fully engages the slot 142 of the spacer 102.

When the inserter instrument 200 is connected to the spacer 102 and the inserter instrument is in the fully extended state, the holes 132, 143 receive the jaws 210 of the shaft 202, the slot 142 of the spacer 102 receives the tab 234 of the wedge 206, the hole 256 of the drill guide 208 is aligned with the hole 126, the hole 259 is aligned with the hole 129, and the hole 260 is aligned with the hole 130. In an alternative embodiment with the spacer shown in FIGS. 2, 3, and 8 and a corresponding drill guide 208, the right drill guide hole is aligned with the fourth hole 128 of the spacer 102. Referring to FIG. 11, the superior side 110 of the wedge 206 is elevated superiorly above the superior serrations 144. Referring to FIGS. 10-14, the inserter instrument 200 connects to the spacer 102 so that the inferior side 112 of the spacer is left entirely exposed. There is no inferior tab comparable to tab 234 to affect the inferior serrations 144. No portion of the inserter instrument 200 extends over any portion of the inferior side 112 or inferior serrations 144. This may apply to the fully retracted state, the fully extended state, and/or the intermediate state.

When the inserter instrument 200 is connected to the spacer 102, the inserter instrument may be actuated to move the inserter instrument from the fully extended state toward the intermediate state so that the tab 234 of the wedge 206 slides completely out of the slot 142 of the spacer 102 while the jaws 210 remain fixed in the holes 132, 134.

The inserter instrument 200 may be disconnected from the spacer 102 by actuating the inserter instrument to move the inserter instrument from the fully extended state toward the fully retracted state so that the tab 234 of the wedge 206 moves completely out of the slot 142 of the spacer 102 and the jaws 210 open to release the spacer 102 and exit the holes 132, 134.

Figure 5:
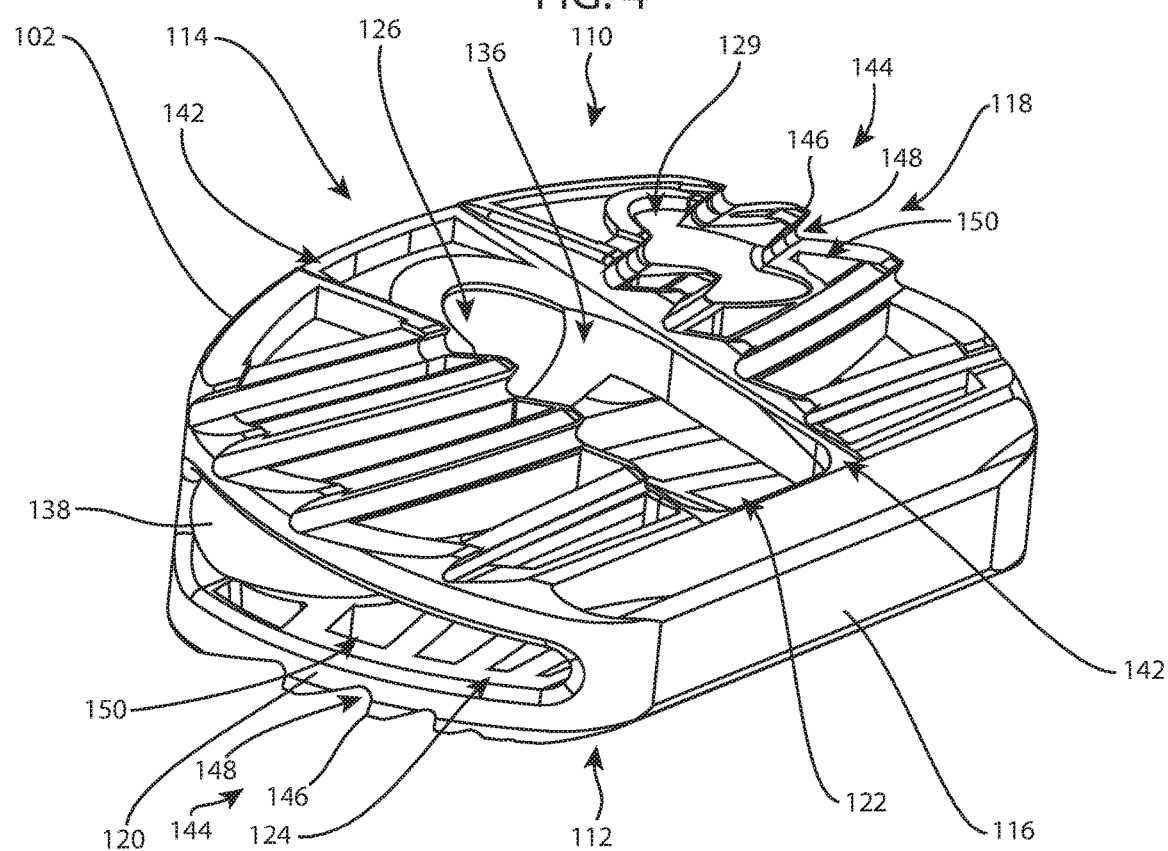
FIG. 5 is an oblique view of the intervertebral cage of FIG. 4, showing superior, posterior, and left sides of the intervertebral cage.
Figure 6:
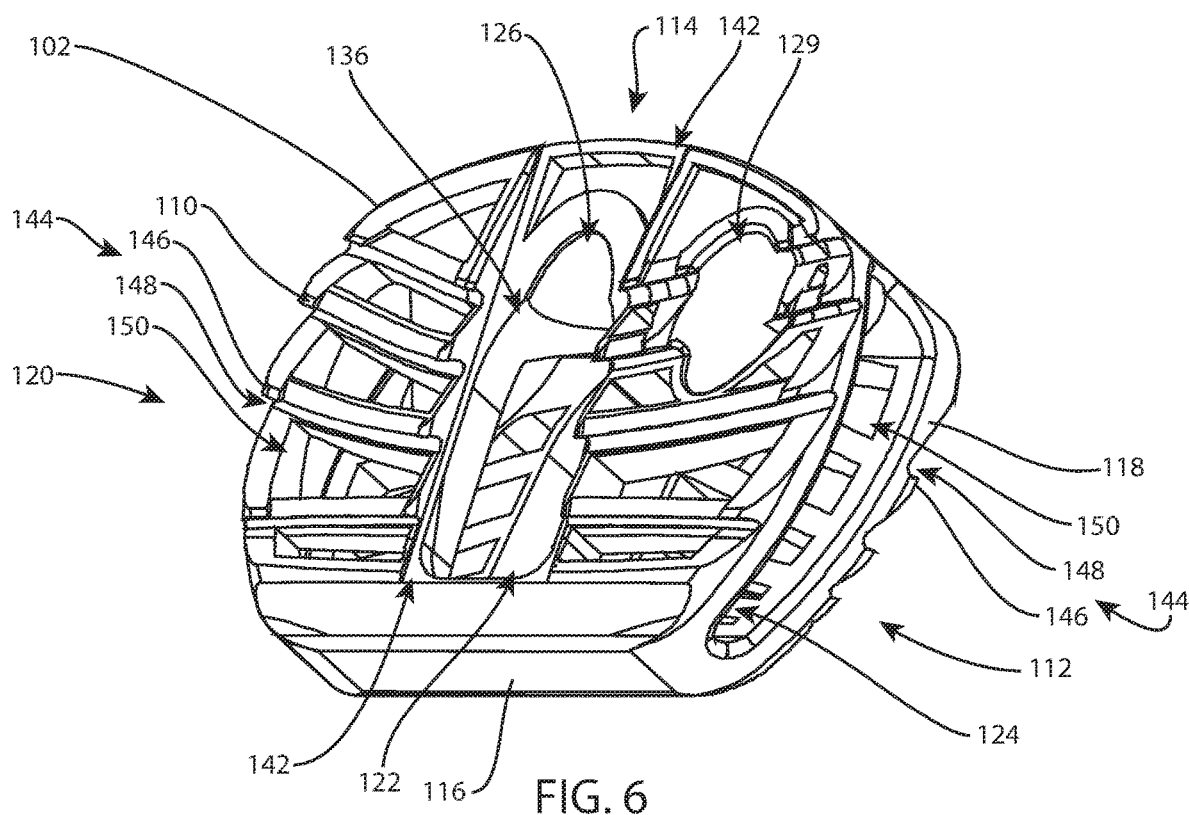
FIG. 6 is another oblique view of the intervertebral cage of FIG. 4, showing superior, posterior, and right sides of the intervertebral cage.
Figure 7:
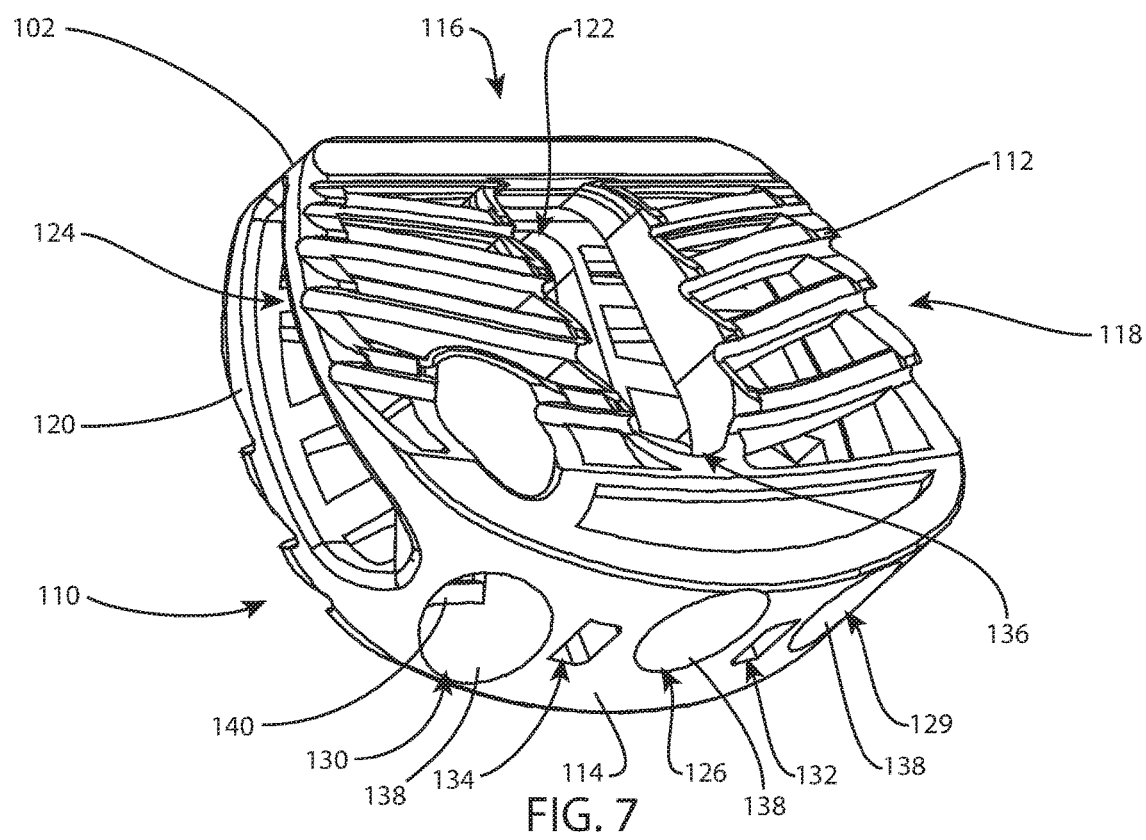
FIG. 7 is yet another oblique view of the intervertebral cage of FIG. 4, showing inferior, anterior, and right sides of the intervertebral cage.

The spacer 102 and inserter instrument 200 represent one example according to certain principles of the disclosed technology. When the tab 234 is in the slot 142, the superior side 110 of the tab 234 is elevated superiorly above the superior side 110 of the spacer, including the corresponding superior serrations 144. In use, as described below, the tab 234 distracts the superior vertebra slightly above the superior side 110 and superior serrations 144 of the spacer 102 so that the spacer 102 can slide easily into the intervertebral space. The tab 234 reduces friction on the superior side 110 of the spacer 102, as compared to the much higher friction between the superiorly- and posteriorly-angled superior serrations 144 and a superior vertebra when inserting the spacer 102 into an intervertebral space. This distraction or friction-reducing function may be provided by other structures or features. In one example, an inserter instrument may include a plate or sheet element that extends over the superior tips of the superior serrations of a spacer with no slot similar to slot 142. In another example, the plate or sheet element may include one or more inferiorly-extending ribs that do engage corresponding slots along the superior side of a spacer. In yet another example, multiple tabs like tab 234 and multiple slots like slot 142 may be present. In yet another example, the inserter instrument may include a structure such as an arm or presser foot that extends into an interior cavity of a spacer, wherein the inserter instrument is actuatable to move the structure superiorly to protrude superiorly past the superior serrations to reduce friction on the superior side of the spacer, and actuatable to move the structure inferiorly to be retracted within the interior cavity. Referring briefly to FIG. 5, the structure may protrude from, and withdraw within, the hole 122 on the superior side 110. The structure may have a complementary shape to the hole 122. In the spacer 102 and inserter instrument 200, as well as these other examples, the friction-reducing feature has an engaged state that reduces friction on the superior side of the spacer the spacer and a disengaged state in which the friction-reducing feature is spaced apart from or retracted away from the spacer so that the full friction of the superior side of the spacer is manifested. The systems provide an initial spacer insertion state that reduces friction at the superior spacer/vertebra interface, and a secondary spacer insertion state that exposes the superior side of the spacer, which is designed to have directional high friction at the superior spacer/vertebra interface (for example, high friction when the spacer 102 attempts to move posteriorly relative to the superior vertebra, due to the orientation of the superior serrations 144).

A method of surgery with the implant assembly 100 and inserter instrument 200 may include one or more of the following steps in any order.

Exposing a surgical approach to the spine. The approach may be an anterior approach, suitable for the example implants and instruments disclosed in this application. The approach may alternatively be a lateral, posterior, or oblique (antero-lateral, postero-lateral) approach, suitable for modified versions of the disclosed implants and instruments.

Performing at least a partial discectomy between first and second adjacent vertebrae, or between a vertebra and a sacrum. A thorough or complete discectomy may be performed.

Preparing the adjacent endplates of the vertebrae or vertebra and sacrum. This step may involve rasping, abrading, resecting, or otherwise removing at least a thin layer of material from each endplate to expose bleeding bone.

Determining a desired superior-inferior height, anterior-posterior length, right-left width, and/or lordotic/kyphotic/scoliotic correction angle for the spacer 102 to be implanted in the prepared intervertebral disc space. This step may involve the use of one or more trials or sizers in the prepared intervertebral space.

Selecting a spacer 102 having the corresponding superior-inferior height, anterior-posterior length, right-left width, and/or lordotic/kyphotic/scoliotic correction angle from a group or kit of spacers having various dimensions.

Connecting the selected spacer 102 to the inserter instrument 200 with the inserter instrument in the fully extended state.

Filling the interior cavity 136 of the spacer 102 with bone graft material. Natural or artificial bone graft material may be used. Other therapeutic agents may be used in conjunction with bone graft material, or used alone.

Inserting the spacer 102 into the prepared intervertebral space from anterior to posterior to a first position, with the superior side 110 facing superiorly and the inferior side 112 facing inferiorly, until the anterior side 114 of the spacer 102 is adjacent to, even with, or aligned with, the anterior aspect of the superior vertebra, or until the anterior side 114 of the spacer 102 is anteriorly displaced relative to the anterior aspect of the inferior vertebra or sacrum by a distance similar to or equal to the slip distance. In the first position, the anterior side 114 of the spacer 102 may be exactly even with the anterior aspect of the superior vertebra, or the anterior side of the spacer may be offset from the anterior aspect of the superior vertebra within a surgically acceptable tolerance. Optionally, in the first position, the anterior side of the spacer may be recessed posteriorly past the anterior aspect of the superior vertebra; this may be the case when partial correction of spondylolisthesis is planned. The anterior side 114 of the spacer 102 may overhang the anterior side of the inferior vertebra. In this step, the spacer 102 may move posteriorly relative to the superior and inferior vertebrae. This step may include impacting the anterior side 114 of the inserter instrument 200 with a mallet to advance the spacer 102 into the prepared intervertebral space. In this step, the superior side 110 of the tab 234 of the wedge 206, which is elevated superiorly above the superior serrations 144 of the spacer 102, slides against the superior vertebral endplate. Thus there is minimal resistance to spacer insertion at the interface between the superior side 110 of the connected spacer 102 and inserter instrument 200 and the superior vertebral endplate. Furthermore, the inferior serrations 144 of the spacer 102 are angled inferiorly and anteriorly so that they present minimal resistance to spacer insertion at the interface between the inferior side 112 of the connected spacer 102 and inserter instrument 200 and the inferior vertebral/sacral endplate.

In this specification, in the context of the methods disclosed herein, "adjacent" is defined as a first structure or feature having a displacement relative to a second structure or feature, wherein the displacement is equal to a preoperatively or intraoperatively planned displacement, taking into account surgically acceptable tolerances of position. In a non-limiting example, the anterior side of the spacer would be adjacent to the anterior aspect of the superior vertebra in the first position even if the horizontal displacement between the anterior side of the spacer and the anterior aspect of the superior vertebra was greater than zero millimeters, such as 1 mm anterior or posterior.

Pausing insertion and retracting the wedge 206 to remove the tab 234 from the slot 142 of the spacer so that the superior serrations 144 dig into the superior vertebral endplate. This step may include actuating the inserter instrument 200 to move the inserter instrument from the fully extended state to the intermediate state so that the tab 234 of the wedge 206 moves completely out of the slot 142 of the spacer 102 while the jaws 210 remain clamped within the holes 132, 134 of the spacer. The tab 234 may move partially or completely out of the intervertebral space. Disengaging the tab 234 from the spacer 102 noticeably increases resistance to spacer insertion at the interface between the superior side 110 of the spacer 102 and the superior vertebral endplate so that the superior vertebra will be carried posteriorly along with the spacer 102 in the next step, when insertion resumes.

Resuming inserting the spacer 102 into the prepared intervertebral space from anterior to posterior to a second position, wherein the superior vertebra moves together with the spacer 102 from anterior to posterior relative to the inferior vertebra or sacrum to decrease, reduce, or eliminate the slip distance. In other words, the superior vertebra moves toward its normal anatomic position relative to the inferior vertebra. In this step, the superior serrations 144 grip the superior vertebra and push it posteriorly, while the inferior serrations still present minimal resistance to spacer insertion at the interface between the inferior side 112 of the spacer 102 and the inferior vertebral/sacral endplate.

When the anterior aspect of the superior vertebra, the anterior side 114 of the spacer 102, and the anterior aspect of the inferior vertebra or sacrum are satisfactorily aligned, stopping advancing the spacer 102. In this step, the anterior side 114 of the spacer 102 is adjacent to, even with, or aligned with, the anterior sides of the superior and inferior vertebrae, and the superior vertebra is in its normal anatomic position relative to the inferior vertebra. Referring briefly to FIG. 1, one will appreciate that in this step, due at least to the normal anatomical lordotic and kyphotic curves of the spine, alignment of the anterior side 114 of the spacer 102 and the anterior aspects of the superior and inferior vertebrae does not necessarily mean that these three features are aligned with zero relative displacement. Rather, in view of the definition of "adjacent" set forth above, these three features are aligned according to pre- and intra-operative planning, and the normal anatomical position and alignment of the superior and inferior vertebrae, within a surgically acceptable tolerance. Furthermore, one will appreciate that in this step, the superior vertebra may move toward its normal anatomical position to partially correct the existing spondylolisthesis without reaching the perfect anatomical position. This may be due to factors such as bony interference or soft tissue contracture that inhibit or prevent complete correction, or risk of neurological or vascular compromise if complete correction were pursued. In this step, the superior vertebra may end in a corrected position relative to the inferior vertebra which is closer to the normal anatomical position than its starting position was. The spacer 102 may end in a second position in which the spacer is inset within the intervertebral space rather than being even with the anterior aspects of the superior and inferior vertebrae. Any one of the anterior, posterior, right, or left sides 114, 116, 118, 120 may be adjacent to corresponding sides of the superior and inferior vertebrae, depending upon the direction of vertebral displacement.

Actuating a drill bit through the holes 256, 126; 258, 128 or 259, 129; and 260, 130 and into the corresponding vertebra or sacrum to prepare holes to receive fasteners.

Inserting fasteners, such as bone screws 104, 106, 108 through the holes 256, 126; 258, 128 or 259, 129; and 260, 130 and into the corresponding vertebra or sacrum to fix the implant assembly 100 in the intervertebral space. This step may include locking each fastener to the spacer 102.

Disconnecting the inserter instrument 200 from the spacer 102 and removing the inserter instrument 200 from the surgical site. This step may include actuating the inserter instrument 200 to move the inserter instrument from the intermediate state to the fully retracted state so that the jaws 210 open sufficiently to release the spacer 102 and exit the holes 132, 134.

Optionally implanting additional components, such as a bone plate or pedicle screw and rod system, to further stabilize the treated spinal level and optionally further reduce the spondylolisthesis.

Closing the surgical approach to the spine.

Another method of surgery with the implant assembly 100 and inserter instrument 200 may include one or more of the following steps in any order. This method may be adapted for conditions where implant migration is to be limited or prevented in the absence of appreciable spondylolisthesis.

Exposing a surgical approach to the spine.

Performing at least a partial discectomy between first and second adjacent vertebrae, or between a vertebra and a sacrum.

Preparing the adjacent endplates of the vertebrae or vertebra and sacrum. Determining a desired superior-inferior height, anterior-posterior length, right-left width, and/or lordotic/kyphotic/scoliotic correction angle for the spacer 102 to be implanted in the prepared intervertebral disc space.

Selecting a spacer 102 having the corresponding superior-inferior height, anterior-posterior length, right-left width, and/or lordotic/kyphotic/scoliotic correction angle from a group or kit of spacers having various dimensions.

Connecting the selected spacer 102 to the inserter instrument 200 with the inserter instrument in the fully extended state.

Filling the interior cavity 136 of the spacer 102 with bone graft material.

Inserting the spacer 102 into the prepared intervertebral space to a final implanted position. In this step, the spacer 102 may move posteriorly relative to the superior and inferior vertebrae. This step may include impacting the anterior side 114 of the inserter instrument 200 with a mallet to advance the spacer 102 into the prepared intervertebral space. In this step, the superior side 110 of the tab 234 of the wedge 206, which is elevated superiorly above the superior serrations 144 of the spacer 102, slides against the superior vertebral endplate.

Retracting the wedge 206 to remove the tab 234 from the slot 142 of the spacer so that the superior serrations 144 dig into the superior vertebral endplate. This step may include actuating the inserter instrument 200 to move the inserter instrument from the fully extended state to the intermediate state so that the tab 234 of the wedge 206 moves completely out of the slot 142 of the spacer 102 while the jaws 210 remain clamped within the holes 132, 134 of the spacer. The tab 234 may move partially or completely out of the intervertebral space.

Actuating a drill bit through the holes 256, 126; 258, 128 or 259, 129; and 260, 130 and into the corresponding vertebra or sacrum to prepare holes to receive fasteners.

Inserting fasteners, such as bone screws 104, 106, 108 through the holes 256, 126; 258, 128 or 259, 129; and 260, 130 and into the corresponding vertebra or sacrum to fix the implant assembly 100 in the intervertebral space. This step may include locking each fastener to the spacer 102.

Disconnecting the inserter instrument 200 from the spacer 102 and removing the inserter instrument 200 from the surgical site. This step may include actuating the inserter instrument 200 to move the inserter instrument from the intermediate state to the fully retracted state so that the jaws 210 open sufficiently to release the spacer 102 and exit the holes 132, 134.

Optionally implanting additional components, such as a bone plate or pedicle screw and rod system, to further stabilize the treated spinal level and optionally further reduce the spondylolisthesis.

Closing the surgical approach to the spine.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A system for spinal surgery in an intervertebral space between a superior vertebra and an inferior vertebra, comprising:
an implant for implantation in the intervertebral space, wherein the implant comprises a superior side for contacting the superior vertebra, an opposite inferior side for contacting the inferior vertebra, and an instrument connection feature; and
an instrument comprising an implant connection feature and a friction-reducing feature, wherein the instrument is connectable to the implant, wherein the instrument comprises first, second, and third states;
wherein in the first state, the implant connection feature is in an unlocked state and the friction-reducing feature is in a disengaged state, wherein in the unlocked state, the implant connection feature is not fixed to the instrument connection feature, wherein when the instrument is connected to the implant and the friction-reducing feature is in the disengaged state, the friction-reducing feature is spaced apart from the implant so that no portion of the instrument extends over the superior side of the implant;
wherein in the second state, the implant connection feature is in a locked state and the friction-reducing feature is in an engaged state, wherein when the instrument is connected to the implant and the implant connection feature is in the locked state, the implant connection feature is fixed to the instrument connection feature, wherein when the instrument is connected to the implant and the friction-reducing feature is in the engaged state, the friction-reducing feature engages the superior side of the implant in a manner that reduces overall friction of insertion of the implant between the superior vertebra and the inferior vertebra;
wherein when the instrument is connected to the implant and the instrument is in the second state, no portion of the instrument extends over the inferior side of the implant;
wherein in the third state, the implant connection feature is in the locked state and the friction-reducing feature is in the disengaged state.

2. The system of claim 1, wherein when the instrument is connected to the implant, no portion of the instrument extends over the inferior side of the implant.

3. The system of claim 1, wherein the friction-reducing feature is a tab of the instrument, wherein when the instrument is connected to the implant and the tab is in the engaged state, the tab protrudes superiorly beyond the superior side of the implant to reduce friction on the superior side of the implant.

4. The system of claim 3, wherein the implant comprises a slot extending across the superior side of the implant, when the instrument is connected to the implant and the tab is in the engaged state, the tab is received in the slot.

5. The system of claim 4, wherein when the instrument goes between the second and third states, the tab slides relative to the slot.

6. A system for spinal surgery in an intervertebral space between a superior vertebra and an inferior vertebra, the system comprising:
an implant for implantation in the intervertebral space, the implant comprising:
a superior side configured to contact the superior vertebra;
an opposite inferior side configured to contact the inferior vertebra; and
an instrument connection feature; and
an instrument comprising:
an implant connection feature connectable to the instrument connection feature; and
a friction-reducing feature comprising:
an engaged state in which the friction-reducing feature covers at least part of the superior side in a manner that reduces overall friction between the superior side and the superior vertebra; and
a disengaged state in which the friction-reducing feature is withdrawn such that the friction-reducing feature does not reduce the overall friction;
wherein in both of the engaged state and the disengaged state the inferior side of the implant remains exposed.

7. The system of claim 6, wherein when the instrument is connected to the implant and the friction-reducing feature is in the engaged state, no portion of the instrument extends over the inferior side of the implant.

8. The system of claim 6, wherein the friction-reducing feature is a tab of the instrument, wherein when the instrument is connected to the implant and the tab is in the engaged state, the tab protrudes superiorly beyond the superior side of the implant to reduce friction on the superior side of the implant.

9. The system of claim 8, wherein the implant comprises a slot extending across the superior side of the implant, wherein when the instrument is connected to the implant and the tab is in the engaged state, the tab is received in the slot.

10. The system of claim 9, wherein when the tab goes between the engaged state and the disengaged state, the tab slides relative to the slot.

11. The system of claim 6, wherein:
the superior side comprises superior teeth that extend superiorly to engage the superior vertebra; and
in the engaged state, the friction-reducing feature prevents the superior teeth from fully engaging the superior vertebra.

12. The system of claim 6, wherein:
the instrument connection feature is on a trailing end of the implant;
the superior side comprises superior teeth that extend superiorly to engage the superior vertebra; and
the superior teeth are oriented generally away from the trailing end.

13. The system of claim 12, wherein:
the inferior side comprises inferior teeth that extend inferiorly to engage the inferior vertebra; and
the inferior teeth are oriented generally toward from the trailing end.

14. A system for spinal surgery in an intervertebral space between a superior vertebra and an inferior vertebra, the system comprising:
an implant for implantation in the intervertebral space, the implant comprising:
a superior side configured to contact the superior vertebra;
an opposite inferior side configured to contact the inferior vertebra; and
an instrument connection feature; and
an instrument comprising:
an implant connection feature connectable to the instrument connection feature; and
a friction-reducing feature comprising:
an engaged state in which the friction-reducing feature covers at least part of the superior side in a manner that reduces friction between the superior side and the superior vertebra; and
a disengaged state in which the friction-reducing feature is withdrawn such that the friction-reducing feature does not reduce the friction;
wherein, in the engaged state, the instrument does not cover any part of the inferior side.

15. The system of claim 14, wherein:
the friction-reducing feature is a tab of the instrument;
when the instrument is connected to the implant and the tab is in the engaged state, the tab protrudes superiorly beyond the superior side of the implant to reduce friction on the superior side of the implant;
the implant comprises a slot extending across the superior side of the implant;
when the instrument is connected to the implant and the tab is in the engaged state, the tab is received in the slot; and
when the tab goes between the engaged state and the disengaged state, the tab slides relative to the slot.

16. The system of claim 14, wherein:
the superior side comprises superior teeth that extend superiorly to engage the superior vertebra;
the inferior side comprises inferior teeth that extend inferiorly to engage the inferior vertebra;
in the engaged state, the friction-reducing feature prevents the superior teeth from fully engaging the superior vertebra;
the instrument connection feature is on a trailing end of the implant;
the superior teeth are oriented generally away from the trailing end; and
the inferior teeth are oriented generally toward from the trailing end.

17. A system for spinal surgery in an intervertebral space between a superior vertebra and an inferior vertebra, the system comprising:
an implant for implantation in the intervertebral space, the implant comprising:
a superior side configured to contact the superior vertebra;
an opposite inferior side configured to contact the inferior vertebra; and
an instrument connection feature; and an instrument comprising:
an implant connection feature connectable to the instrument connection feature; and
a friction-reducing feature comprising:
an engaged state in which the friction-reducing feature covers at least part of the superior side in a manner that reduces friction between the superior side and the superior vertebra; and
a disengaged state in which the friction-reducing feature is withdrawn such that the friction-reducing feature does not reduce the friction;
wherein:
the superior side defines a superior profile;
the inferior side defines an inferior profile; and
in the engaged state, the friction-reducing feature extends superiorly beyond at least part of the superior profile and the inferior profile is left exposed to the inferior vertebra.

18. The system of claim 17, wherein:
the friction-reducing feature is a tab of the instrument;
the implant comprises a slot extending across the superior side of the implant;
when the instrument is connected to the implant and the tab is in the engaged state, the tab is received in the slot; and
when the tab goes between the engaged state and the disengaged state, the tab slides relative to the slot.

19. The system of claim 17, wherein:
the superior side comprises superior teeth that extend superiorly to engage the superior vertebra;
the inferior side comprises inferior teeth that extend inferiorly to engage the inferior vertebra;
in the engaged state, the friction-reducing feature prevents the superior teeth from fully engaging the superior vertebra;
the instrument connection feature is on a trailing end of the implant;
the superior teeth are oriented generally away from the trailing end; and
the inferior teeth are oriented generally toward from the trailing end.

20. A system for spinal surgery in an intervertebral space between a superior vertebra and an inferior vertebra, the system comprising:
an implant for implantation in the intervertebral space, the implant comprising:
a superior side configured to contact the superior vertebra;
an opposite inferior side configured to contact the inferior vertebra; and
an instrument connection feature; and
an instrument comprising:
an implant connection feature connectable to the instrument connection feature; and
a friction-reducing feature comprising:
an engaged state in which the friction-reducing feature covers at least part of the superior side in a manner that reduces friction between the superior side and the superior vertebra; and
a disengaged state in which the friction-reducing feature is withdrawn such that the friction-reducing feature does not reduce the friction;
wherein:
the superior side comprises superior teeth that extend superiorly to engage the superior vertebra;
the inferior side comprises inferior teeth that extend inferiorly to engage the inferior vertebra; and
in the engaged state, the friction-reducing feature prevents the superior teeth from fully engaging the superior vertebra while allowing the inferior teeth to engage the inferior vertebra.

21. The system of claim 20, wherein:
the friction-reducing feature is a tab of the instrument;
when the instrument is connected to the implant and the tab is in the engaged state, the tab protrudes superiorly beyond the superior side of the implant to reduce friction on the superior side of the implant;
the implant comprises a slot extending across the superior side of the implant;
when the instrument is connected to the implant and the tab is in the engaged state, the tab is received in the slot; and
when the tab goes between the engaged state and the disengaged state, the tab slides relative to the slot.

22. The system of claim 20, wherein:
the inferior side comprises inferior teeth that extend inferiorly to engage the inferior vertebra;
the instrument connection feature is on a trailing end of the implant;
the superior teeth are oriented generally away from the trailing end; and
the inferior teeth are oriented generally toward from the trailing end.

* * * * *